(12) United States Patent
Pipenhagen et al.

(10) Patent No.: US 9,282,953 B2
(45) Date of Patent: Mar. 15, 2016

(54) SYSTEMS AND METHODS FOR LOCATING AND CLOSING A TISSUE PUNCTURE

(75) Inventors: Catherine A. Pipenhagen, Chanhassen, MN (US); Jyue Boon Lim, New Brighton, MN (US); Neil J. Modeland, Gladewater, TX (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 916 days.

(21) Appl. No.: 11/967,979

(22) Filed: Dec. 31, 2007

(65) Prior Publication Data

US 2009/0171281 A1  Jul. 2, 2009

(51) Int. Cl.
*A61B 17/03* (2006.01)
*A61B 17/00* (2006.01)

(52) U.S. Cl.
CPC .................. *A61B 17/0057* (2013.01)

(58) Field of Classification Search
CPC ................. A61B 17/0057; A61B 2017/00557; A61B 2017/0065; A61B 2017/00672; A61B 2017/00654
USPC ........... 606/65, 200, 213–217, 232, 310, 313, 606/326, 327; 604/14–18, 59–64
See application file for complete search history.

(56) References Cited

U.S. PATENT DOCUMENTS

| | | |
|---|---|---|
| 4,317,445 A | 3/1982 | Robinson |
| 4,744,364 A | 5/1988 | Kensey |
| 4,890,612 A | 1/1990 | Kensey |
| 5,021,059 A | 6/1991 | Kensey et al. |
| 5,061,274 A | 10/1991 | Kensey |
| 5,108,421 A * | 4/1992 | Fowler .......................... 606/213 |
| 5,192,300 A | 3/1993 | Fowler |
| 5,192,302 A | 3/1993 | Kensey et al. |
| 5,222,974 A | 6/1993 | Kensey et al. |
| 5,275,616 A | 1/1994 | Fowler |
| 5,282,827 A | 2/1994 | Kensey et al. |
| 5,290,310 A | 3/1994 | Makower et al. |
| 5,292,332 A | 3/1994 | Lee |
| 5,304,184 A | 4/1994 | Hathaway et al. |
| 5,306,254 A | 4/1994 | Nash et al. |
| 5,312,435 A | 5/1994 | Nash et al. |
| 5,320,639 A | 6/1994 | Rudnick |
| 5,326,350 A | 7/1994 | Li |
| 5,334,216 A | 8/1994 | Vidal et al. |
| 5,342,393 A | 8/1994 | Stack |
| 5,354,271 A | 10/1994 | Voda |
| 5,368,601 A | 11/1994 | Sauer et al. |
| 5,383,896 A | 1/1995 | Gershony et al. |

(Continued)

OTHER PUBLICATIONS

International Search Report, PCT/US2008/013967, Apr. 3, 2009.

*Primary Examiner* — Kathleen Holwerda
(74) *Attorney, Agent, or Firm* — Holland & Hart

(57) ABSTRACT

A vascular closure device includes a main body and an expandable portion that can be selectively expanded and contracted. The vascular closure device may be used to close the hole in a wall of a vessel after a medical procedure. For example, the vascular closure device may be used to close the hole in an artery after a medical procedure that required access to the artery. In one embodiment, the expandable portion may be oriented at an oblique angle relative to the main body. This may be desirable in situations where the vessel puncture is oriented at an angle relative to the vessel. Orienting the expandable portion at an oblique angle relative to the main body may help the expandable portion to cover the hole in the wall of the vessel.

21 Claims, 19 Drawing Sheets

(56) References Cited

U.S. PATENT DOCUMENTS

| | | | |
|---|---|---|---|
| 5,383,897 | A | 1/1995 | Wholey |
| 5,383,899 | A | 1/1995 | Hammerslag |
| RE34,866 | E | 2/1995 | Kensey et al. |
| 5,391,183 | A | 2/1995 | Janzen et al. |
| 5,403,328 | A | 4/1995 | Shallman |
| 5,403,329 | A | 4/1995 | Hinchcliffe |
| 5,405,354 | A | 4/1995 | Sarrett |
| 5,411,520 | A * | 5/1995 | Nash et al. .................. 606/213 |
| 5,417,699 | A | 5/1995 | Klein et al. |
| 5,419,765 | A * | 5/1995 | Weldon .............. A61B 17/0057 604/507 |
| 5,431,639 | A * | 7/1995 | Shaw ............................ 604/264 |
| 5,431,666 | A | 7/1995 | Sauer et al. |
| 5,437,631 | A | 8/1995 | Janzen |
| 5,443,481 | A | 8/1995 | Lee |
| 5,462,561 | A * | 10/1995 | Voda .................. A61B 17/0057 112/169 |
| 5,478,352 | A | 12/1995 | Fowler |
| 5,486,195 | A * | 1/1996 | Myers et al. .................. 606/213 |
| 5,496,332 | A | 3/1996 | Sierra et al. |
| 5,496,335 | A | 3/1996 | Thomason et al. |
| 5,507,744 | A | 4/1996 | Tay et al. |
| 5,507,758 | A | 4/1996 | Thomason et al. |
| 5,527,322 | A | 6/1996 | Klein et al. |
| 5,531,759 | A | 7/1996 | Kensey et al. |
| 5,545,178 | A | 8/1996 | Kensey et al. |
| 5,549,633 | A | 8/1996 | Evans et al. |
| 5,554,106 | A | 9/1996 | Layman-Spillar et al. |
| 5,571,181 | A | 11/1996 | Li |
| 5,591,205 | A | 1/1997 | Fowler |
| 5,593,422 | A | 1/1997 | Muijs Van De Moer et al. |
| 5,601,602 | A | 2/1997 | Fowler |
| 5,601,603 | A | 2/1997 | Illi |
| 5,613,974 | A | 3/1997 | Andreas et al. |
| 5,620,461 | A | 4/1997 | Muijs Van De Moer et al. |
| 5,626,601 | A | 5/1997 | Gershony et al. |
| 5,643,318 | A | 7/1997 | Tsukernik et al. |
| 5,645,566 | A | 7/1997 | Brenneman et al. |
| 5,649,959 | A | 7/1997 | Hannam et al. |
| 5,653,730 | A | 8/1997 | Hammerslag |
| 5,662,681 | A | 9/1997 | Nash et al. |
| 5,665,106 | A | 9/1997 | Hammerslag |
| 5,674,231 | A | 10/1997 | Green et al. |
| 5,676,689 | A | 10/1997 | Kensey et al. |
| 5,681,334 | A | 10/1997 | Evans et al. |
| 5,700,277 | A | 12/1997 | Nash et al. |
| 5,716,375 | A | 2/1998 | Fowler |
| 5,725,498 | A | 3/1998 | Janzen et al. |
| 5,725,551 | A | 3/1998 | Myers et al. |
| 5,728,122 | A | 3/1998 | Leschinsky et al. |
| 5,728,132 | A | 3/1998 | Van Tassel et al. |
| 5,728,133 | A | 3/1998 | Kontos |
| 5,728,134 | A | 3/1998 | Barak |
| 5,741,223 | A | 4/1998 | Janzen et al. |
| 5,746,755 | A | 5/1998 | Wood et al. |
| 5,755,727 | A | 5/1998 | Kontos |
| 5,759,194 | A | 6/1998 | Hammerslag |
| 5,766,183 | A | 6/1998 | Sauer |
| 5,766,206 | A | 6/1998 | Wijkamp et al. |
| 5,782,861 | A | 7/1998 | Cragg et al. |
| 5,792,173 | A | 8/1998 | Breen et al. |
| 5,810,810 | A | 9/1998 | Tay et al. |
| 5,810,846 | A | 9/1998 | Virnich et al. |
| 5,810,884 | A | 9/1998 | Kim |
| 5,814,065 | A | 9/1998 | Diaz |
| 5,820,631 | A | 10/1998 | Nobles |
| 5,827,299 | A | 10/1998 | Thomason et al. |
| 5,830,130 | A | 11/1998 | Janzen et al. |
| 5,843,124 | A | 12/1998 | Hammerslag |
| 5,853,421 | A | 12/1998 | Leschinsky et al. |
| 5,855,559 | A | 1/1999 | Van Tassel et al. |
| 5,855,585 | A | 1/1999 | Kontos |
| 5,860,990 | A | 1/1999 | Nobles et al. |
| 5,861,004 | A | 1/1999 | Kensey et al. |
| 5,861,005 | A | 1/1999 | Kontos |
| 5,868,762 | A | 2/1999 | Cragg et al. |
| 5,868,778 | A | 2/1999 | Gershony et al. |
| 5,876,411 | A | 3/1999 | Kontos |
| 5,902,311 | A | 5/1999 | Andreas et al. |
| 5,906,631 | A | 5/1999 | Imran |
| 5,910,155 | A | 6/1999 | Ratcliff et al. |
| 5,919,207 | A | 7/1999 | Taheri |
| 5,941,897 | A | 8/1999 | Myers |
| 5,951,583 | A | 9/1999 | Jensen et al. |
| 5,957,952 | A * | 9/1999 | Gershony et al. ............. 606/213 |
| 5,964,782 | A | 10/1999 | Lafontaine et al. |
| 5,976,161 | A | 11/1999 | Kirsch et al. |
| 5,980,539 | A | 11/1999 | Kontos |
| 5,997,555 | A | 12/1999 | Kontos |
| 6,007,562 | A | 12/1999 | Harren et al. |
| 6,007,563 | A | 12/1999 | Nash et al. |
| 6,017,359 | A | 1/2000 | Gershony et al. |
| 6,024,747 | A | 2/2000 | Kontos |
| 6,033,401 | A | 3/2000 | Edwards et al. |
| 6,033,427 | A | 3/2000 | Lee |
| 6,036,721 | A | 3/2000 | Harren et al. |
| 6,042,601 | A | 3/2000 | Smith |
| 6,045,569 | A | 4/2000 | Kensey et al. |
| 6,048,357 | A | 4/2000 | Kontos |
| 6,048,358 | A | 4/2000 | Barak |
| 6,056,768 | A * | 5/2000 | Cates .................. A61B 17/0057 280/14.21 |
| 6,063,085 | A | 5/2000 | Tay et al. |
| 6,071,300 | A | 6/2000 | Brenneman et al. |
| 6,077,279 | A | 6/2000 | Kontos |
| 6,090,130 | A | 7/2000 | Nash et al. |
| 6,110,184 | A | 8/2000 | Weadock |
| 6,120,524 | A | 9/2000 | Taheri |
| 6,126,675 | A * | 10/2000 | Shchervinsky et al. ....... 606/213 |
| 6,136,010 | A | 10/2000 | Modesitt et al. |
| 6,139,556 | A | 10/2000 | Kontos |
| 6,162,192 | A | 12/2000 | Cragg et al. |
| 6,174,322 | B1 | 1/2001 | Schneidt |
| 6,179,863 | B1 | 1/2001 | Kensey et al. |
| 6,183,496 | B1 | 2/2001 | Urbanski |
| 6,193,670 | B1 | 2/2001 | Van Tassel et al. |
| 6,197,042 | B1 | 3/2001 | Ginn et al. |
| 6,206,895 | B1 | 3/2001 | Levinson |
| 6,231,561 | B1 | 5/2001 | Frazier et al. |
| 6,245,080 | B1 | 6/2001 | Levinson |
| 6,296,658 | B1 | 10/2001 | Gershony et al. |
| 6,398,796 | B2 | 6/2002 | Levinson |
| 6,425,911 | B1 | 7/2002 | Akerfeldt et al. |
| 6,425,924 | B1 | 7/2002 | Rousseau |
| 6,508,828 | B1 | 1/2003 | Akerfeldt et al. |
| 6,547,806 | B1 | 4/2003 | Ding |
| 6,569,185 | B2 | 5/2003 | Ungs |
| 6,596,012 | B2 | 7/2003 | Akerfeldt et al. |
| 6,596,014 | B2 | 7/2003 | Levinson et al. |
| 6,626,918 | B1 * | 9/2003 | Ginn et al. .................... 606/148 |
| 6,682,489 | B2 | 1/2004 | Tenerz et al. |
| 6,712,837 | B2 | 3/2004 | Akerfeldt et al. |
| 6,743,195 | B2 | 6/2004 | Zucker |
| 6,860,895 | B1 | 3/2005 | Akerfeldt et al. |
| 6,929,655 | B2 | 8/2005 | Egnelov et al. |
| 2005/0107826 | A1 | 5/2005 | Zhu et al. |
| 2005/0149117 | A1 | 7/2005 | Khosravi et al. |
| 2005/0228443 | A1 | 10/2005 | Yassinzadeh |
| 2007/0156084 | A1 | 7/2007 | Belhe et al. |

* cited by examiner

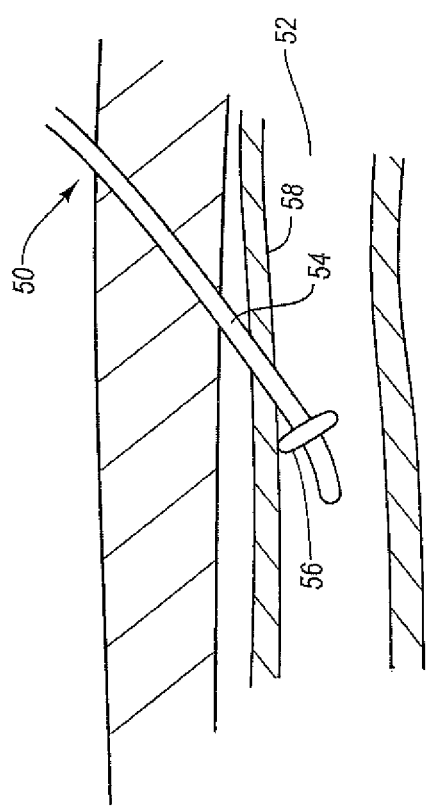
FIG. 1
(Conventional)
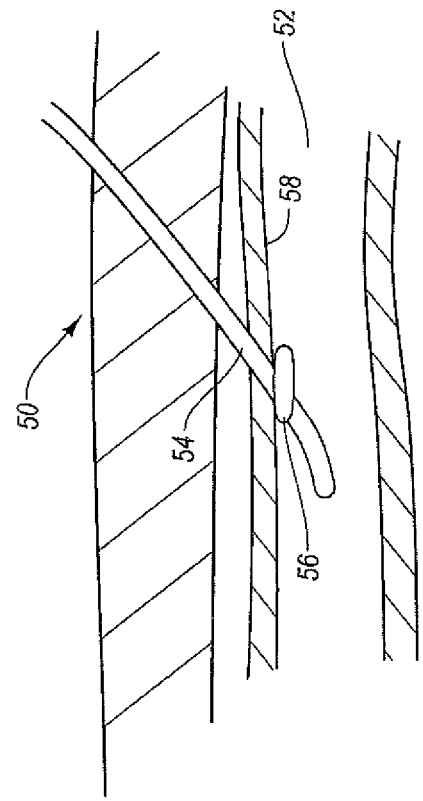
FIG. 2
(Conventional)

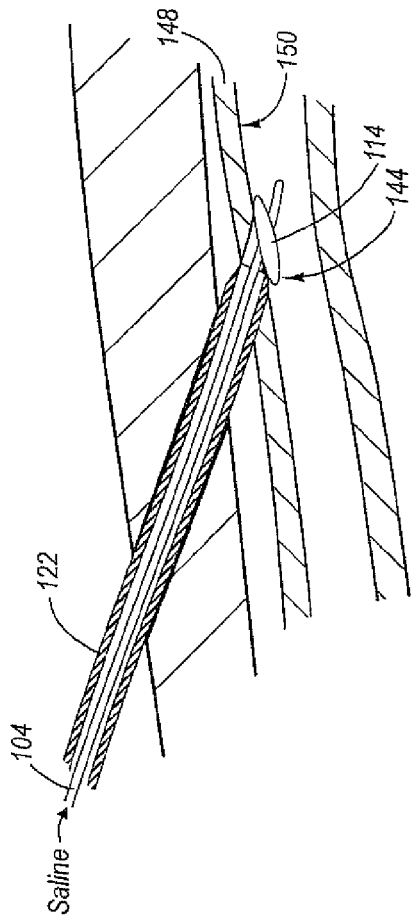
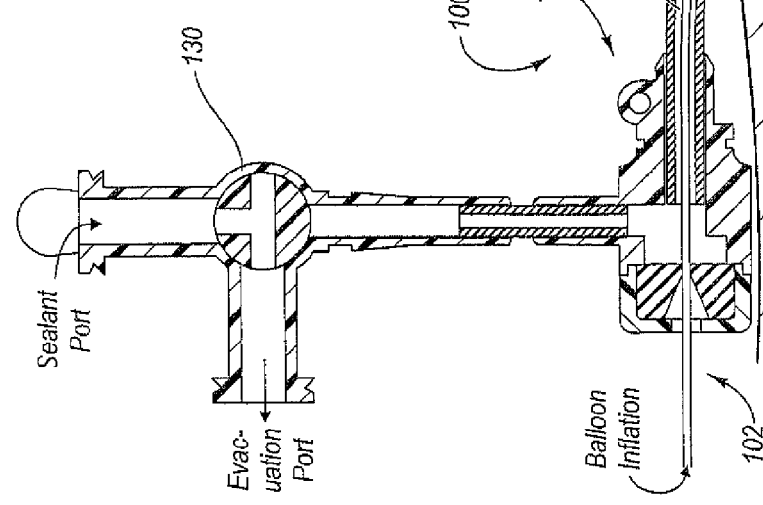
FIG. 5
FIG. 6

SYSTEMS AND METHODS FOR LOCATING AND CLOSING A TISSUE PUNCTURE

CROSS-REFERENCE TO RELATED PATENT APPLICATIONS

U.S. patent application Ser. No. 11/325,206, entitled "Balloon Insertion Apparatus and Method of Sealing a Tissue Puncture," filed on 4 Jan. 2006, is incorporated herein by reference in its entirety. In the event of a conflict, the subject matter explicitly recited or shown herein controls over any subject matter incorporated by reference. All definitions of a term (express or implied) contained in any of the subject matter incorporated by reference herein are hereby disclaimed. The paragraphs shortly before the claims dictate the meaning to be given to any term explicitly recited herein subject to the disclaimer in the preceding sentence.

BACKGROUND

Various medical procedures, particularly cardiology related procedures, involve accessing a corporeal vessel or other bodily lumen through a percutaneous sheath. Accessing the vessel necessarily requires the formation of a hole or opening in the vessel wall. The hole allows medical equipment such as catheters to be inserted into the vessel so that the physician can perform the desired medical procedure. After the medical procedure has been completed, the sheath must eventually be removed from the vessel and the access hole in the vessel wall must be closed.

Historically, access holes to blood vessels were closed by applying prolonged manual pressure over the puncture site by a physician or other trained medical professional. In most situations, the time involved was extensive, especially if anticoagulants and/or thrombolytic agents were used during the procedure. Using manual pressure to close the access holes resulted in greater time demands on the medical professional and also increased the patient's recovery time. Consequently, the expense associated with the procedure also increased. The discomfort and delay in mobilization for patients resulting from this prolonged manual pressure is significant.

In response to these problems, a number of vascular closure devices have been developed to close an access hole in a vessel wall more efficiently. For example, an access opening in the vessel wall may be closed by positioning a resorbable sealing plug adjacent to the hole or sandwiching the hole between the sealing plug and an anchor. These devices have been found to be highly effective, but they may not be suitable for every situation. Also, these devices leave the anchor in the vessel, which may not be desirable in certain situations. In an effort to overcome some of these aspects of current vascular closure devices, closure devices utilizing balloons have been investigated. These closure devices may be used to close an access hole to a blood vessel by inserting the balloon through the opening in the vessel wall, inflating the balloon, pulling the balloon against the inner wall of the vessel, introducing a sealing material to the external side of the hole in the vessel wall, and withdrawing the balloon catheter.

Unfortunately, there are a number of problems associated with using balloon type closure devices. As illustrated in FIGS. 1 and 2, one of the problems associated with these closure devices is that the balloon does not contact the vessel wall in a uniform manner. FIGS. 1 and 2 show a vascular closure device 50 inserted into a blood vessel 52. The vascular closure device 50 includes a body 54 and a balloon 56 positioned perpendicular to the body 54. As the balloon 56 is pulled up against the wall 58, the uppermost tip contacts the wall 58 first. As the balloon 56 is pulled further, increasing amounts of the balloon 56 contact the wall 58 until finally the entire balloon 56 is in contact with the wall 58 as shown in FIG. 2. Because the balloon 56 contacts the wall 58 in this way, the balloon 56 often deforms as shown in FIG. 2 resulting in a poor seal between the balloon 56 and the wall 58 of the blood vessel 52. The poor seal may allow the sealing material to pass through the hole in the blood vessel 52 and into the bloodstream. Also, it is difficult for the physician or other medical professional to determine when the balloon 56 is in position since the balloon 56 tends to provide a similar amount of tactile feedback from the time the balloon 56 first contacts the wall 58 and the time the balloon 56 is fully in position as shown in FIG. 2. The lack of reliable tactile feedback has caused physicians, in some instances, to pull so hard on the balloon 56 that the balloon 56 ruptures or pulls through the hole in the blood vessel 52.

The problems with vascular closure devices that utilize balloons have greatly hindered commercial acceptance of these type of products. Accordingly, it would be advantageous to provide an improved vascular closure device that utilizes a balloon.

SUMMARY

A number of embodiments of vascular closure devices are described herein. The vascular closure devices may be used to close a hole in a blood vessel following a medical procedure or injury. For example, the vascular closure devices may be used to close a hole used to access the vascular system of a patient during a medical procedure such as angioplasty, electrophysiology study, and the like. It should be appreciated that the vascular closure devices may also be used to close any hole in a vessel regardless of whether the hole was made intentionally (e.g., vascular access hole used during a medical procedure) or accidentally (e.g., an accident that results in a punctured blood vessel).

A vascular closure device may include a main body and an expandable portion positioned at a distal end of the main body. The expandable portion of the vascular closure device may be configured to be inserted through the hole and into the vessel. The expandable portion may then be expanded and moved into contact with the inner wall of the vessel to block the hole. A sealing material may be applied to an area adjacent to the exterior of the hole. In one embodiment, the sealing material may flow over the hole as well as the area adjacent to the exterior of the hole. Once the sealing material is sufficiently in place, the expandable portion may be contracted and removed from the vessel.

The expandable portion may be oriented at an oblique angle relative to the main body when the expandable portion is in an expanded configuration. Since the main body is often inserted into the vessel at an oblique angle, this orientation results in the expandable portion being parallel to the inner wall of the vessel. As the expandable portion is pulled into contact with the inner wall, the expandable portion contacts the vessel wall uniformly. The physician is able to tactilely determine when the expandable portion is in contact with the inner wall of the vessel. Also, the expandable portion forms a uniform seal all the way around the hole so that sealing material and the like do not leak into vessel.

The vascular closure device may have any of a number of configurations. For example, in one embodiment, the expandable portion may be made from any suitable elastomeric material. In one embodiment, the expandable portion may be made, at least in part, from a resilient elastomeric material such as polyurethanes and/or silicone. The expandable portion may be coupled to a cylindrical tube (e.g., hypotube) that is used to direct fluid to the expandable portion. The fluid may be used to selectively expand and contract the expandable portion. Any suitable fluid may be used for this purpose such as saline, carbon dioxide gas, etc. The expandable portion may also be coupled to a tube such as a nitinol hypotube. Also, a guidewire may extend distally from the expandable portion to render the distal end of the vascular closure device atraumatic.

The foregoing and other features, utilities, and advantages of the subject matter described herein will be apparent from the following more particular description of certain embodiments as illustrated in the accompanying drawings.

DRAWINGS

The accompanying drawings illustrate various embodiments of the vascular closure devices and are a part of the specification. The illustrated embodiments are intended to be merely examples of certain embodiments of the vascular closure devices.

FIGS. 1 and 2 show a conventional vascular closure device that utilizes a balloon to close a hole in a blood vessel.

FIG. 5 is a sectional side elevation view of one embodiment of a patient with the introducer sheath of FIG. 3 positioned within an arteriotomy and the associated vascular closure device extending through the introducer sheath and into a blood vessel.

FIG. 6 is a sectional side elevation view of the patient, introducer sheath, and vascular closure device of FIG. 5 where an expandable portion of the vascular closure device is in an expanded configuration and in contact with the inner wall of the arteriotomy.

Throughout the drawings, identical reference numbers designate similar, but not necessarily identical, elements.

DETAILED DESCRIPTION

A number of embodiments of vascular closure devices are described herein that may be used to close a hole in a blood vessel. It should be appreciated that although the vascular closure devices may be used to close any hole in any animal, the following discussion focuses on vascular closure devices that are used to close a hole in a blood vessel such as an arteriotomy. It should be appreciated, however, that the principles, concepts, and features described herein may apply to numerous other settings and may be used in connection with other uses beyond closing vascular holes (e.g., urinary tract, digestive tract, and the like). Also, it should be appreciated, that the features, advantages, characteristics, etc. of one embodiment may be applied to any other embodiment to form an additional embodiment unless noted otherwise.

As mentioned above, many medical procedures are performed that require access to a blood vessel through a hole, puncture, or opening in the vessel. The vascular closure devices described herein may be used to seal the hole in the blood vessel or arteriotomy following completion of the medical procedure. In most situations, the puncture extends through the patients skin and into the vessel at an oblique angle (e.g., approximately 20° to 45°) relative to the vessel. This makes it possible to insert a device such as a catheter into the vessel without bending the catheter significantly or damaging the blood vessel.

In most situations, an introducer sheath extends through the tissue tract and into the blood vessel. The introducer sheath allows the medical personnel to quickly and easily insert different medical devices into the vessel without continually reinserting each device through the skin, underlying tissue, and the vessel. The introducer may be configured to have a blood flow indicator that provides a visual way for medical personnel to readily determine when the introducer has entered the blood vessel. It should be appreciated, however, that a separate device may be used to locate the blood vessel before the introducer sheath is put into position.

Turning to the drawings, a variety of embodiments of vascular closure devices are shown. In some of the embodiments, the sealing material is injected or forced into the tissue tract area near the hole in the blood vessel. In other embodiments, the sealing material may be configured to melt and flow into the tissue tract. Numerous other embodiments of vascular closure devices can be used that have an expandable portion that can be used to deploy sealing material adjacent to the hole in the blood vessel.

Figure 3:
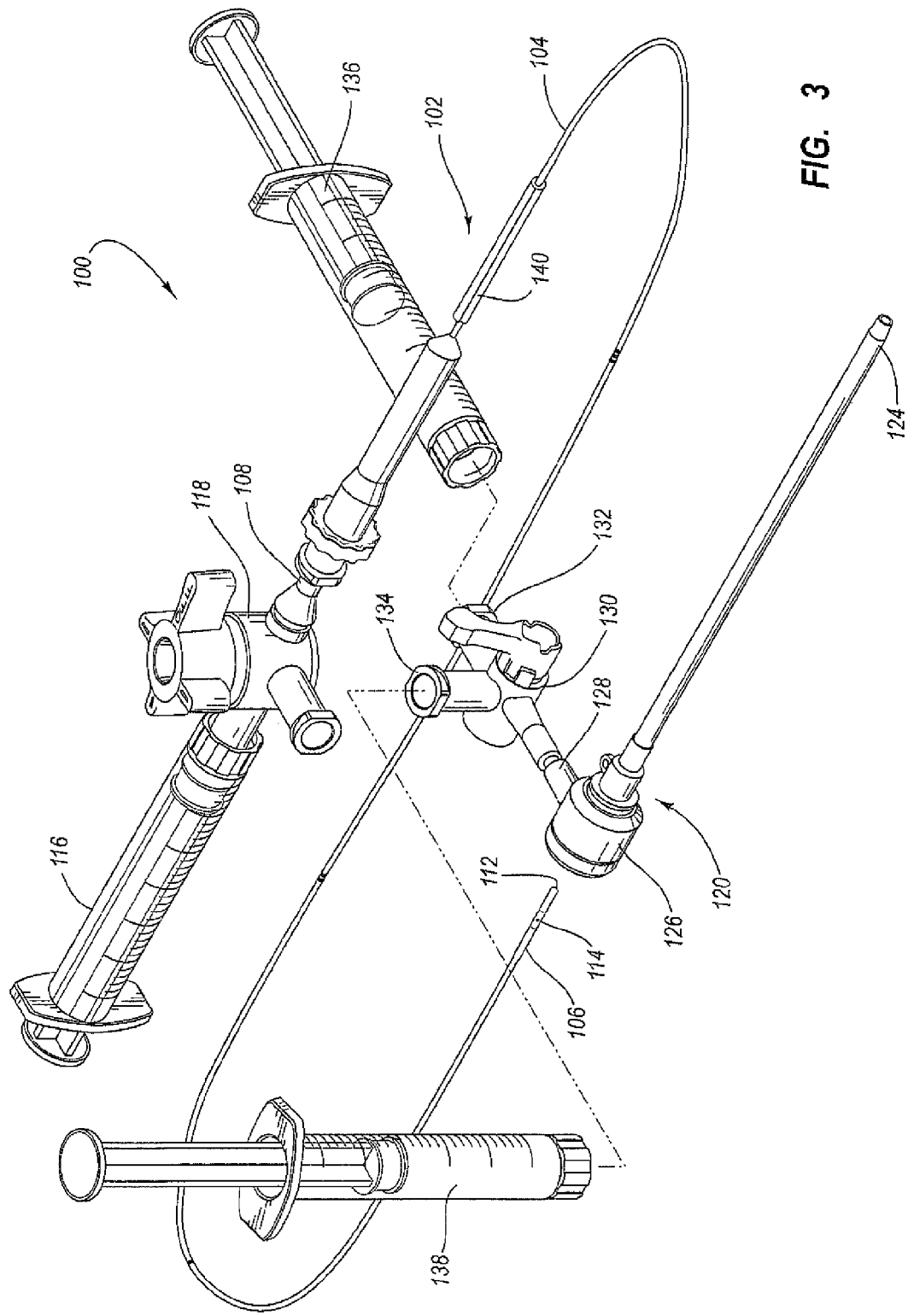
FIG. 3 is an exploded assembly view of one embodiment of an introducer sheath and an associated vascular closure device.

Referring now to FIG. 3, one embodiment of a vascular closure device 100 (alternatively referred to herein as a vascular closure device, vascular puncture closure device, tissue puncture closure device, or internal tissue puncture sealing apparatus) is shown. The vascular closure device 100 includes an elongated main body or conduit 102, a fluid dispenser 116, and a valve assembly 118. The main body or balloon catheter 102 has a distal or first end 106 and a proximate or second end 108. The proximate end 108 is coupled to the valve assembly 118, which is in turn coupled to the fluid dispenser 116. A distal tip 112 is provided on the distal end 106 of the main body 102. An expandable portion 114 (alternatively referred to herein as a balloon or inflatable portion) is also positioned at the distal end 106 of the main body 102.

It should be noted that for purposes of this disclosure, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature.

It should be appreciated that the configuration of the vascular closure device 100 may be altered in any of a number of ways such as by adding additional components, removing components, or rearranging components. For example, the valve assembly 118 may be integrated into the fluid dispenser 116 so that the resulting device appears to be a single component, but functions as both a fluid dispenser and a valve. In another embodiment, the valve assembly 118 may be eliminated entirely. Numerous other changes may also be made to the vascular closure device 100.

The expandable portion 114 may be selectively expanded and/or contracted using the fluid from the fluid dispenser 116. The main body 102 may include a lumen or passage 104 that extends from the proximate end 108 of the main body 102 to the expandable portion 114. The lumen 104 is also in fluid communication with the valve assembly 118 and the fluid dispenser 116. Thus, the main body 102 may form a conduit that is capable of delivering a fluid from the fluid dispenser 116 to the expandable portion 114. The fluid may be selectively injected into or suctioned out of the expandable portion 114 to move the expandable portion 114 between an expanded configuration and a contracted configuration. In other words, the expandable portion 114 may be selectively inflated and/or deflated with fluid from the fluid dispenser 116. The valve assembly 118 is positioned between the fluid dispenser 116 and the lumen 104 in the main body 102. The valve assembly 118 can be used to selectively isolate the lumen 104 from the fluid dispenser 116. Accordingly, when the valve assembly 118 is open, the fluid dispenser 116 may be used to expand or inflate the expandable portion 114. Following expansion, the valve assembly 118 may be closed to prevent fluid from flowing back into the fluid dispenser 116 and thus maintain the expandable portion 114 in the expanded configuration. In another embodiment, the valve assembly 118 may be omitted and the fluid dispenser 116 may be configured to provide the necessary force (e.g., friction of parts in the fluid dispenser 116, mechanical lock to hold fluid dispenser 116 in place, and so forth) to prevent the fluid from flowing back from the expandable portion 114 when the fluid dispenser 116 is not being used.

Figure 4:
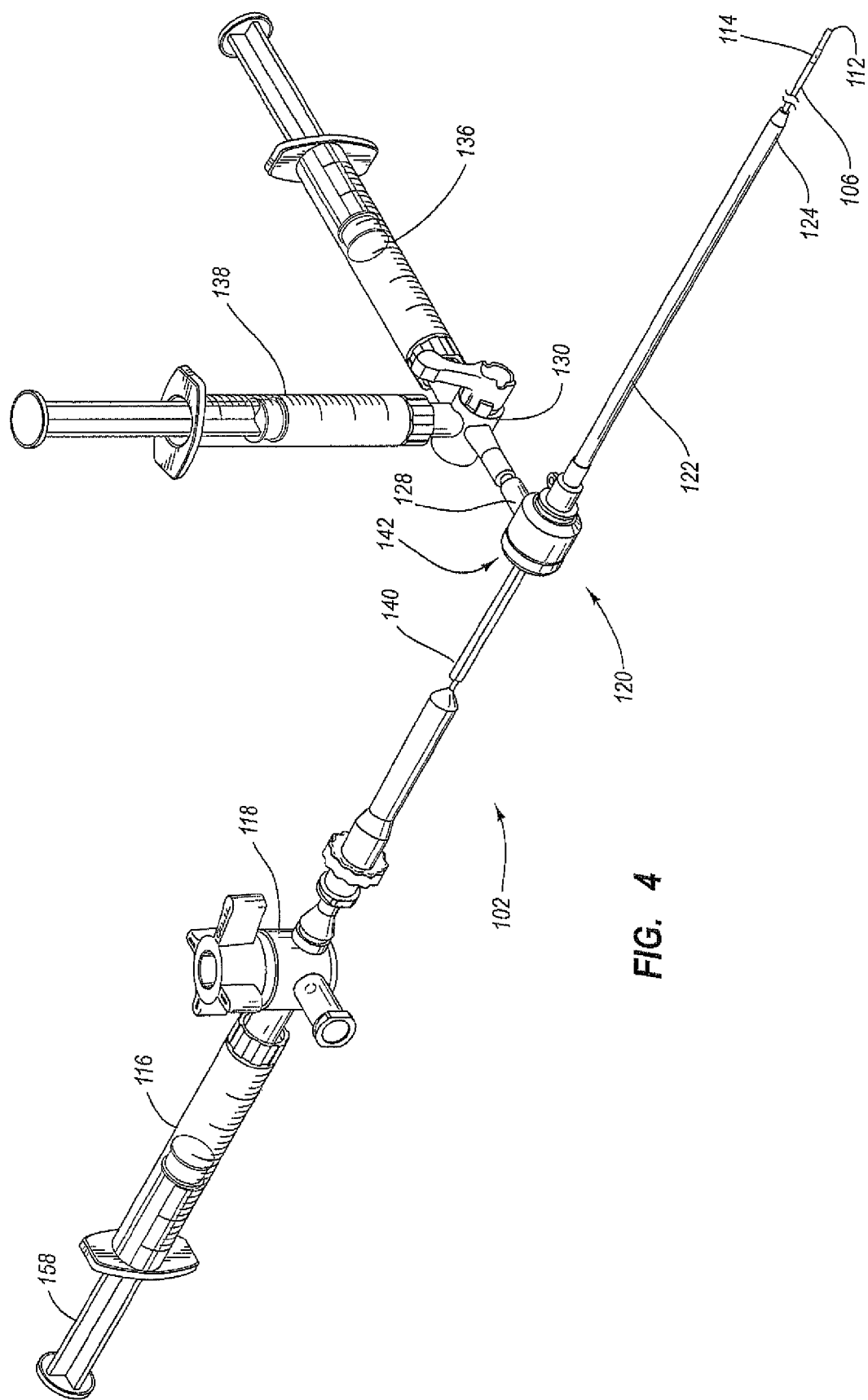
FIG. 4 is a perspective view of the vascular closure device inserted into the introducer sheath.

The fluid dispenser 116 may have any suitable configuration. For example, as shown in FIGS. 3 and 4, the fluid dispenser 116 may include a syringe that is capable of injecting fluid through the lumen 104 and to the expanding portion 114. Other suitable devices or systems may also be used as the fluid dispenser 116. Also, it should be appreciated that the fluid dispenser 116 may be used to dispense any type of suitable fluid. In one embodiment, the fluid provided by the fluid dispenser 116 may include standard saline solution or any other suitable liquid. In another embodiment, the fluid may include a gas such as carbon dioxide or air. Any fluid that is suitable for medical applications may be used to expand and contract the expandable portion 114 of the vascular closure device 110.

The main body 102 may have any suitable configuration and may be made of any suitable material. In one embodiment, the lumen 104 may be formed by a tube such as hypotube. In one embodiment, the hypotube may include one or more shape memory alloys such as nickel-titanium alloys and the like. In other embodiments, the hypotube may include other materials such as stainless steel and the like. The main body 102 may also include a guidewire that extends distally from the expandable portion 114. The main body 102 may also include multiple lumens to deliver a number of fluids to the distal end 106.

The expandable portion 114 may be formed from any suitable expandable material. In one embodiment, the expandable portion 114 includes a resilient expandable portion. Suitable examples of such materials include polyurethanes and/or silicones. In one embodiment, the expandable material used to provide the expandable portion 114 may be attached to the main body 102 using any suitable fastening technique or device. For example, the expandable material may be adhered or glued to the main body 102 so that the lumen 104 is in fluid communication with the interior of the expandable portion 114. Any suitable adhesive may be used for this purpose. Examples of particularly suitable adhesives include cyanoacrylate adhesives (cured with or without a light), acrylic adhesives (cured with or without a light), epoxy adhesives, and the like. In one embodiment, the expandable material may include a urethane balloon available from Advanced Polymers, Salem N.H., as part number 050000030A adhered to nickel-titanium hypotube that is included as part of the main body 102 using any of the following adhesives available from Henkel Corp., Rocky Hill, Conn., as LOCTITE brands 3911 (item number 36536), 3921 (item number 36484), 4011 (item number 18680), or 4061 (item number 18686). In some embodiments, a primer may be applied before the adhesive. A suitable primer may also be obtained from Henkel Corp. as LOCTITE brand 770 (item number 18396). The surface of the hypotube may be etched or roughened in the areas where the adhesive is applied.

It should be appreciated that the main body 102 and the expandable portion 114 may have any of a number of suitable configurations. For example, instead of attaching the expandable portion 114 to the main body 102, the expandable portion 114 may be integrally formed as part of the main body 102. For example, the expandable portion 114 may be injection molded with the remainder of the main body 102. Numerous other embodiments may also be used to provide the main body 102 and the expandable portion 114.

Figure 11:
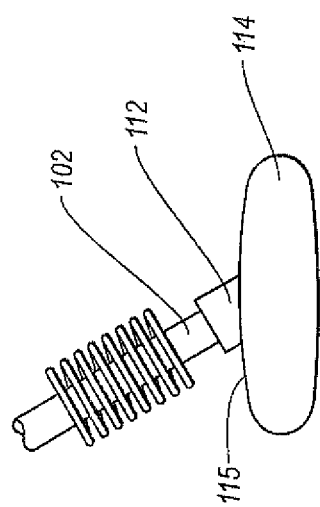
FIG. 11 is a perspective view of one embodiment of a distal end of a main body of the vascular closure device.
Figure 12:
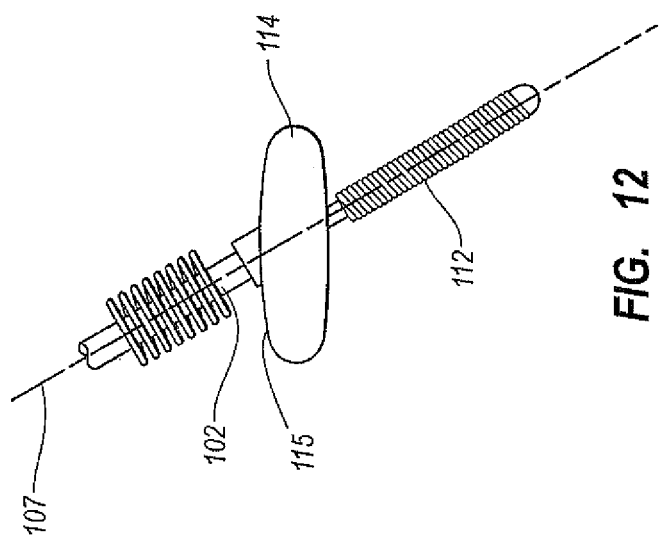
FIG. 12 is a perspective view of another embodiment of a distal end of a main body of the vascular closure device where the expandable portion has a tail when the expandable portion is in an expanded configuration.

Turning to FIGS. 11 and 12, various embodiments of the main body 102 are shown with the expandable portion 114 in the expanded configuration. As shown in these FIGS., the expandable portion 114 is positioned at an oblique angle (e.g., about 20° to 40°) relative to the main body 102. The expandable portion 114 typically has a shape that is not perfectly round. Thus, the expandable portion 114 can have a shape that is spheroidal, ellipsoidal, or the like. It should be appreciated that referring to the expandable portion 114 as being positioned at an oblique angle relative to the main body 102, is meant to confer the general idea that the side 115 of the expandable portion 114 that is intended to contact the inner surface of the vessel is positioned at an oblique angle prior to or without contacting the inner surface of the vessel (e.g., when the expandable portion 114 is in a rest state). The angle between the expandable portion 114 and the main body 102 is determined by measuring the angle between the general longitudinal axis 107 of the main body 102 and the side 115 of the expandable portion 114 that is intended to contact the inner surface of the vessel at the location where the axis 107 and the side 115 are the closest to each other (FIG. 11). The expandable portion 114 may be oriented at an angle of approximately 15° to 55° relative to the main body 102, approximately 20° to 45° relative to the main body 102, or, desirably, approximately 25° to 40° relative to the main body 102.

As shown in FIG. 12, the expandable portion 114 may be positioned so that the distal tip 112 of the main body 102 extends past the expandable portion 114. In this embodiment, the distal tip 112 may be atraumatic to facilitate insertion of the distal end 106 into a blood vessel without damaging or harming the blood vessel. In one embodiment, the distal tip 112 may be formed by a guidewire that is coupled to the expandable portion 114 and/or the main body 102. The guidewire may be surrounded by a spring to make it atraumatic.

FIG. 11 shows another embodiment of the vascular closure device 100 where the expandable portion 114 is positioned on the distal tip 112 of the main body 102 such that the main body 102 terminates at the expandable portion 114. This embodiment may be advantageous because only the deflated expandable portion 114 needs to be withdrawn through the hole after the access hole is sealed.

Referring back to FIG. 3, the vascular closure device 100 also includes an introducer assembly or sheath 120. The introducer sheath 120 includes a valve 130 positioned at a proximal end 126 and an elongated tube or conduit 122 that extends from the valve 130 to a distal end 124. The tube 122 has a lumen 142 (FIG. 5) that is receptive of the main body 102. The introducer sheath 120 also includes at least one opening or side-port 128 positioned at the proximal end 126 that is in fluid communication with the lumen 142. The valve 130 branches to a suction port 132 and a sealing material port 134. It should be appreciated that in other embodiments the suction port 132 and sealing material port 134 may be one and the same so that the valve 130 does not branch.

As shown in FIG. 3, the suction port 132 is in fluid communication with a suction source 136 or other evacuator such as, for example, a syringe. Similarly, the sealing material port 134 is in fluid communication with a supply of sealing material, such as a syringe 138 that contains the sealing material. The valve 130 may comprise a translucent three-way valve that moves between a first or closed position where the suction port 132 and the sealing material port 134 are both isolated from the lumen 142, a second position where the suction port 132 is in fluid communication with the lumen 142, and a third position where the sealing material port 134 is in fluid communication with the lumen 142. Details of the valve 130 and the associated suction port 132 and sealing material port 134 are shown in FIGS. 5-9.

Referring to FIG. 4, the main body 102 may be inserted into the lumen 142 of the introducer sheath 120 as shown. The main body 102 is sized so that it does not fill the entire lumen 142. Thus, the side-port 128 is in fluid communication with the portion of the lumen 142 that is not filled.

A stopper sleeve or spacer 140 is shown disposed over the main body 102 to limit the insertion distance of the main body 102 into the introducer sheath 120. The length of the spacer 140 is chosen so that the distal end 106 of the main body 102 extends beyond the distal end 124 of the introducer sheath 120 by a predetermined distance. According to one embodiment, the predetermined distance is approximately 2.5 cm to 4.0 cm. The distance is chosen to allow the expandable portion 114 of the main body 102 to pass through the introducer sheath 120 and into a blood vessel as discussed in more detail below. The spacer 140 may comprise a split tube of metal or plastic that can be easily removed as desired.

Methods of closing a hole or puncture in a vessel such as an arteriotomy 144 using the vascular closure device 100 are discussed with reference to FIGS. 5-10. Referring first to FIG. 5, the vascular closure device 100 is shown with the introducer sheath 120 inserted through a hole 144 in a blood vessel 148. In one embodiment, the introducer sheath 120 may be used for introducing instruments during the medical procedure as well as to close the hole 144. In other embodiments, another introducer may be used during the procedure. When it is time to close the hole 144, the introducer may be swapped for the introducer sheath 120.

With the introducer sheath 120 in place, the main body 102 may be inserted through the lumen 142 until the expandable portion 114 extends beyond the tip of the distal end 124 of the introducer sheath 120 and into the blood vessel 148. The introducer sheath 120 and main body 102 are oriented at an oblique angle relative to the walls of the blood vessel 148. The main body 102 and expandable portion 114, when positioned in the lumen 142, may restrict passage of other devices or objects through the lumen 142. The expandable portion 114 may be expanded by opening the valve 118 and depressing the fluid dispenser 116. FIG. 5 shows the expandable portion 114 after it has been expanded in the blood vessel 148. Notably, the expandable portion 114 is positioned at an oblique angle relative to the main body 102. The valve 118 may be closed to maintain the expandable portion 114 in an expanded position. The main body 102 and the introducer sheath 120 are retracted until the expandable portion 114 contacts an inner wall 150 of the blood vessel 148 and seals the internal side of the hole 144 as shown in FIG. 6. The expandable portion 114 is positioned so that it is parallel to the inner wall 150 as it moves toward and contacts the inner wall 150. Thus, the expandable portion 114 forms a good seal over the hole 144 and provides sufficient tactile feedback to allow the medical professional to determine when the expandable portion 114 is in position. In one embodiment, the vascular closure device 100 may include a marking or some other indicia to allow the medical personnel to determine the rotational orientation of the main body 102. In this way, the medical personnel can reorient the main body 102 and the expandable portion 114 so that it is parallel to the inner wall 150 before moving the expandable portion 114 into contact with the inner wall 150.

Figure 7:
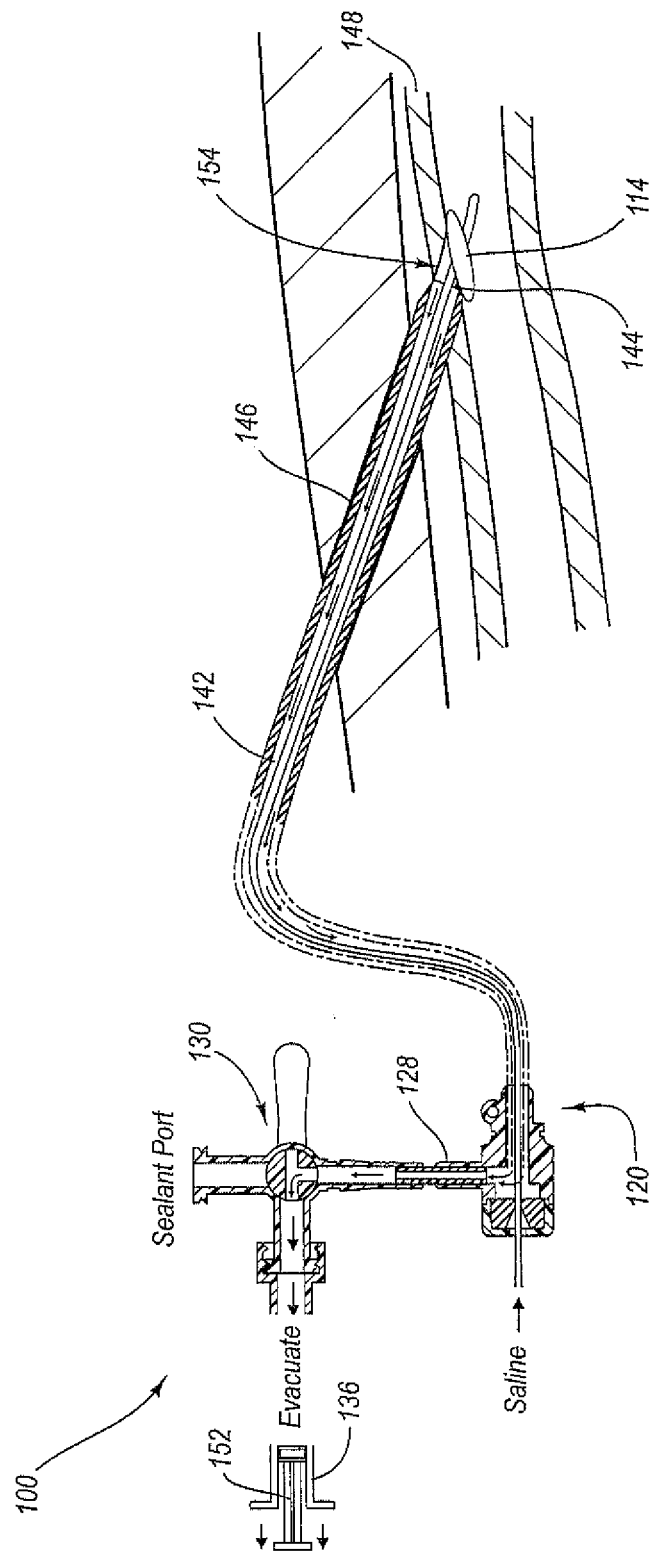
FIG. 7 is a sectional side elevation view of another embodiment of the patient, introducer sheath, and vascular closure device of FIG. 6 shown with the introducer sheath connected to a suction apparatus.

With the expandable portion 114 in place so that it internally blocks or seals the hole 144, the side-port valve 130 is opened to allow fluid communication between the unfilled space of the lumen 142 and the suction source 136 as shown in FIG. 7. The pressure is lowered in the lumen 142 by withdrawing a stem 152 of the suction source 136 (in this embodiment, a syringe) or by some other suction device. As the pressure is lowered in the lumen 142 and communicated to the tissue tract 146, a situs 154 of the hole 144 is aspirated, removing fluids from the tissue tract 146 via the lumen 142.

As the arteriotomy 144 is aspirated, a surgeon or other medical professional may visually inspect the fluid contents evacuated through the translucent valve 130 to assess blood flow through the hole 144. This allows the medical professional to ensure that the introducer sheath 120 and/or the expandable portion 114 are properly positioned within the blood vessel 148. A flow of blood may indicate that the expandable portion 114 is not properly sealing the hole 144.

Figure 8:
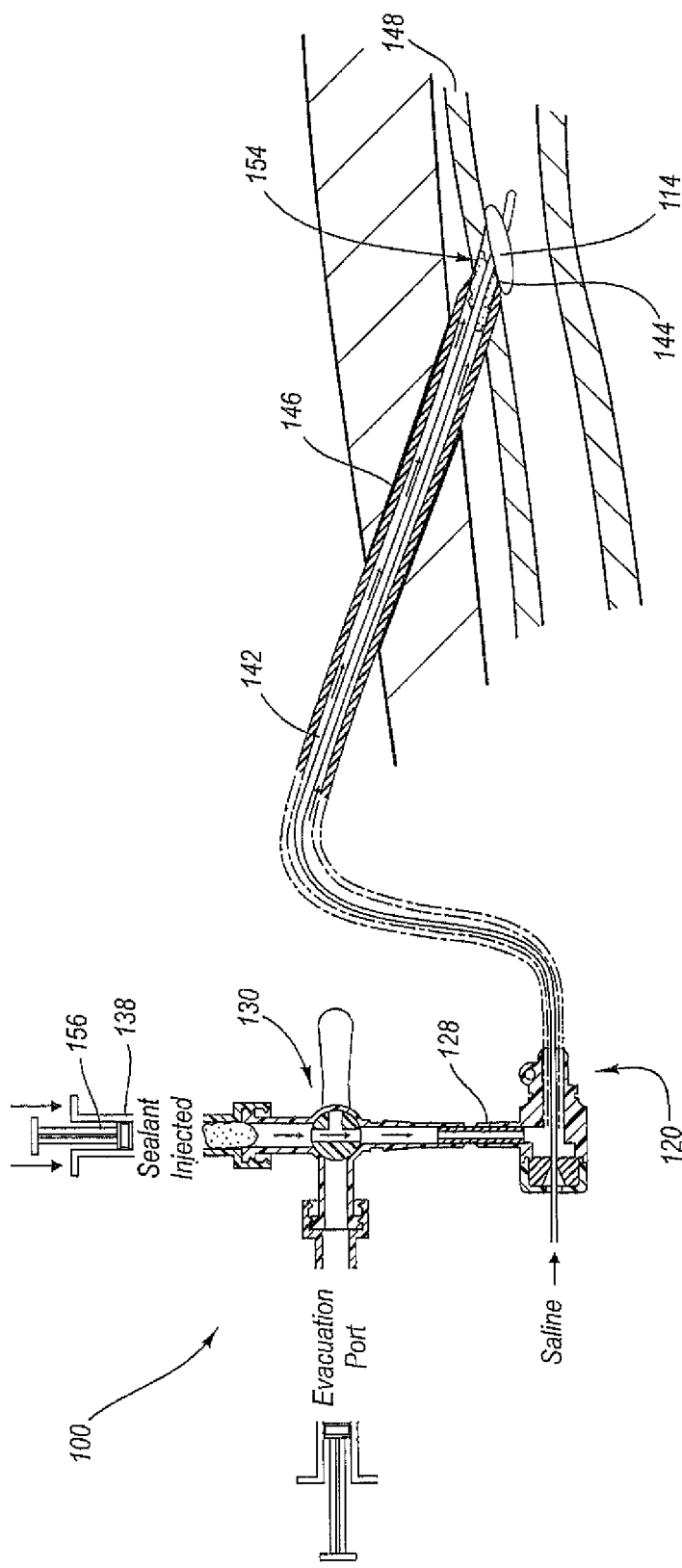
FIG. 8 is a sectional side elevation view of another embodiment of the patient, introducer sheath, and the vascular closure device of FIG. 7 shown with the introducer sheath coupled to a sealant source.

When the surgeon is satisfied with the positioning of the introducer sheath 120 and the expandable portion 114, the valve 130 is toggled to create a fluid communication path between the lumen 142 and the sealing material contained in the syringe 138 or other sealing material supply as shown in FIG. 8. The syringe 138 holds a volume of sealing material that is injected into the introducer sheath 120 via the side-port 128 as a stem 156 is depressed. The sealant flows through the lumen 142 and into the tissue tract 146. Further, because the tissue tract 146 has been evacuated and is in a vacuum condition, the sealing material is drawn through the annulus toward the hole 144. The vacuum condition of the situs 154 external to the hole 144 causes the sealing material to quickly and efficiently fill all of the voids around the hole 144 and in the tissue tract 146. Preferably, the syringe 138 holds a volume of sealing material sufficient to fill the lumen 142 and therefore the tissue tract 146. As the sealing material is injected (FIG. 8), the introducer sheath 120 is preferably withdrawn with respect to the expandable portion 114 to allow the sealing material to fill the tissue tract 146. Therefore, in order to facilitate retraction of the introducer sheath 120, the spacer 140 (FIG. 4) is removed.

Following injection of the sealing material, it may be optionally activated, cured, or set. In many embodiments, the sealing material includes a liquid or gel sealant that includes any of the following thrombin, collagen, fibrin/fibrinogen, cyanoacrylate, polyvinyl alcohol, polyethylene glycol, chitosan, poly-n-acetyl glucosamine, and combinations thereof (e.g., thrombin and collagen, fibrin/fibrinogen and collagen, cyanoacrylate and collagen, or thrombin and fibrin/fibrinogen). In other embodiments, the sealing material may include implants (implant is positioned adjacent to the exterior of the hole 146 using a variety of different techniques). Implants are typically provided as a solid, fiber, compressible foam, or the like while sealants are provided as a liquid, gel, or the like. The sealing material may operate by mechanically blocking the hole in the vessel, reacting with the blood or other nearby tissue to block the hole, or the like. In some embodiments, the sealing material may not be dependent on a biochemical reaction with blood or other bodily fluids to create a hemostatic seal. However, the gels or foams used according to some aspects of the present invention may in some cases be activated or cured by, for example, application of a second fluid, UV light, or other activation mechanisms.

Figure 9:
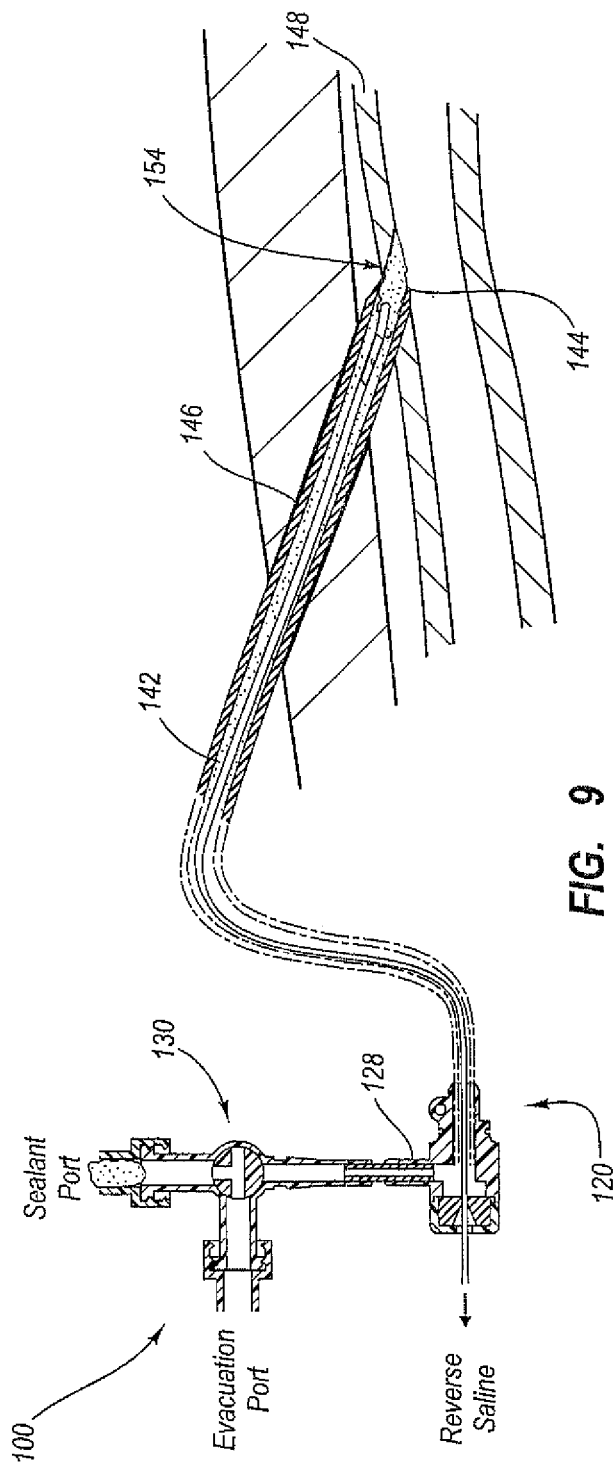
FIG. 9 is a sectional side elevation view of another embodiment of the patient, introducer sheath, and vascular closure device of FIG. 8 with the expandable portion being contracted and being withdrawn through the sealant.
Figure 10:
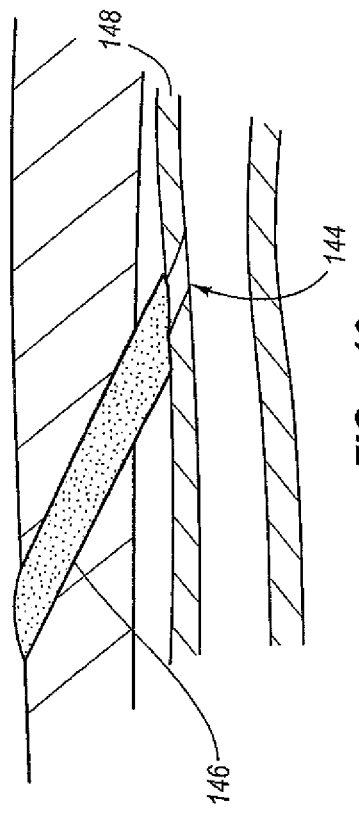
FIG. 10 is a sectional side elevation view of the patient following retraction of the introducer sheath and vascular closure device from the situs of the hole in the blood vessel.

Once the sealing material is in place adjacent the exterior of the hole 144, the expandable portion 114 is contracted as shown in FIG. 9 by reopening the valve 118 (FIG. 4). The stem 158 (FIG. 4) of the fluid dispenser 116 (FIG. 4) may be retracted to ensure fill contraction of the expandable portion 114. The main body 102 and the introduction sheath 120 are retracted, with the expandable portion 114 sliding through the sealing material. According to some embodiments, following removal of the main body 102 and the instruction sheath 120, manual pressure may be applied to the arteriotomy site to counteract any sealing action disruption caused by the act of pulling the expandable portion 114 through the sealing material. However, manual pressure is applied for only a fraction of the time allocated to traditional arteriotomy closures. For example, according to the principles described herein, manual pressure may be applied following retraction of the vascular closure device 100 for only ten minutes or less. The sealing material remains in the tissue tract 146 sealing the arteriotomy 144 as shown in FIG. 10.

Turning now to FIGS. 13-23, another embodiment of a vascular closure device 250 is shown. The vascular closure device 250 may be used to deploy sealing material adjacent to and outside of the hole in the blood vessel. The sealing material functions to block the hole in the blood vessel and/or the tissue tract to stop the bleeding. In one embodiment, the sealing material may be a lipid based sealing material. For example, the sealing material may include monoglycerides of saturated and unsaturated fatty acids. The sealing material may include one or more of such monoglycerides alone or in combination with other materials such as therapeutic agents, additives, and carrier materials. The therapeutic agents may include drugs or other substances that provide local or systemic therapeutic effect in the body. Additives may be included to alter the physical properties such as the melting point, strength, resiliency, etc. of the sealing material.

It should be appreciated that there are a wide number of substances, mixtures, molecules, etc. that may be used as the sealing material. In one embodiment, the sealing material may comprise a monoglyceride including a fatty acid group having 12 to 22 carbon atoms. In another embodiment, the sealing material may include glycerol monooleate, glycerol monostearate, glycerol monopalmitate, glycerol monolaurate, glycerol monocaproate, glycerol monocaprylate, glycerol monolinoleate, glycerol monolinolenate, glycerol monomyristate, and/or glycerol monoarachidonate. Those materials that may be preferable for use as the sealing material include glycerol, monooleate, glycerol monolinoleate, and/or glycerol monolinolenate, in any combination or amount.

The sealing material may melt, gel, or otherwise undergo a phase change when deployed adjacent to the hole in the blood vessel. In order for the sealing material to melt, it is desirable for the sealing material to have a melting point that is less than bodily temperature but high enough that the sealing material is a solid at room temperature. After the sealing material has been inserted into the tissue tract, it is heated by the patient's body until it begins to melt or gel. In one embodiment, the sealing material may have a melting point that is no more than 37° C. In another embodiment, the sealing material may have a melting point that is about 27° C. to 37° C., about 30° C. to 37° C., or about 34° C. to 37° C.

Once the sealing material has melted, it may flow into the tissue tract toward the hole in the blood vessel. At the same time, the sealing material may begin to expand and form a cubic phase due to exposure to bodily fluids. In one embodiment, the sealing material may expand up to 46% of its original size. The sealing material may also exhibit adhesive properties that help to hold the sealing material in place in the tissue tract. The expansion of the sealing material and formation of the cubic phase (the sealing material becomes solid or non-flowable in the cubic phase) may act to hold the sealing material in place over the hole in the blood vessel thereby closing the hole in the blood vessel. It should be appreciated that any of the foregoing sealing materials may also be used with the vascular closure device 110.

The vascular closure devices 250 facilitates deployment of the sealing material in the tissue tract of the patient. The sealing material blocks the tissue tract and stops the bleeding. In one embodiment, the sealing material is bio-absorbable to allow it to be removed by the body's natural processes. In another embodiment, the sealing material may be deployed with and coupled to another bio-absorbable component such as a sealing plug (e.g., collagen plug) or anchor both of which may also be bio-absorbable (e.g., PLA and PGA materials). In one embodiment, the vascular closure device 250 may be configured to not leave any components inside the blood vessel after the closure procedure is over (i.e., an extra-vascular closure device). In this embodiment, the sealing material and any other components left in the patient are outside of the blood vessel.

Figure 13:
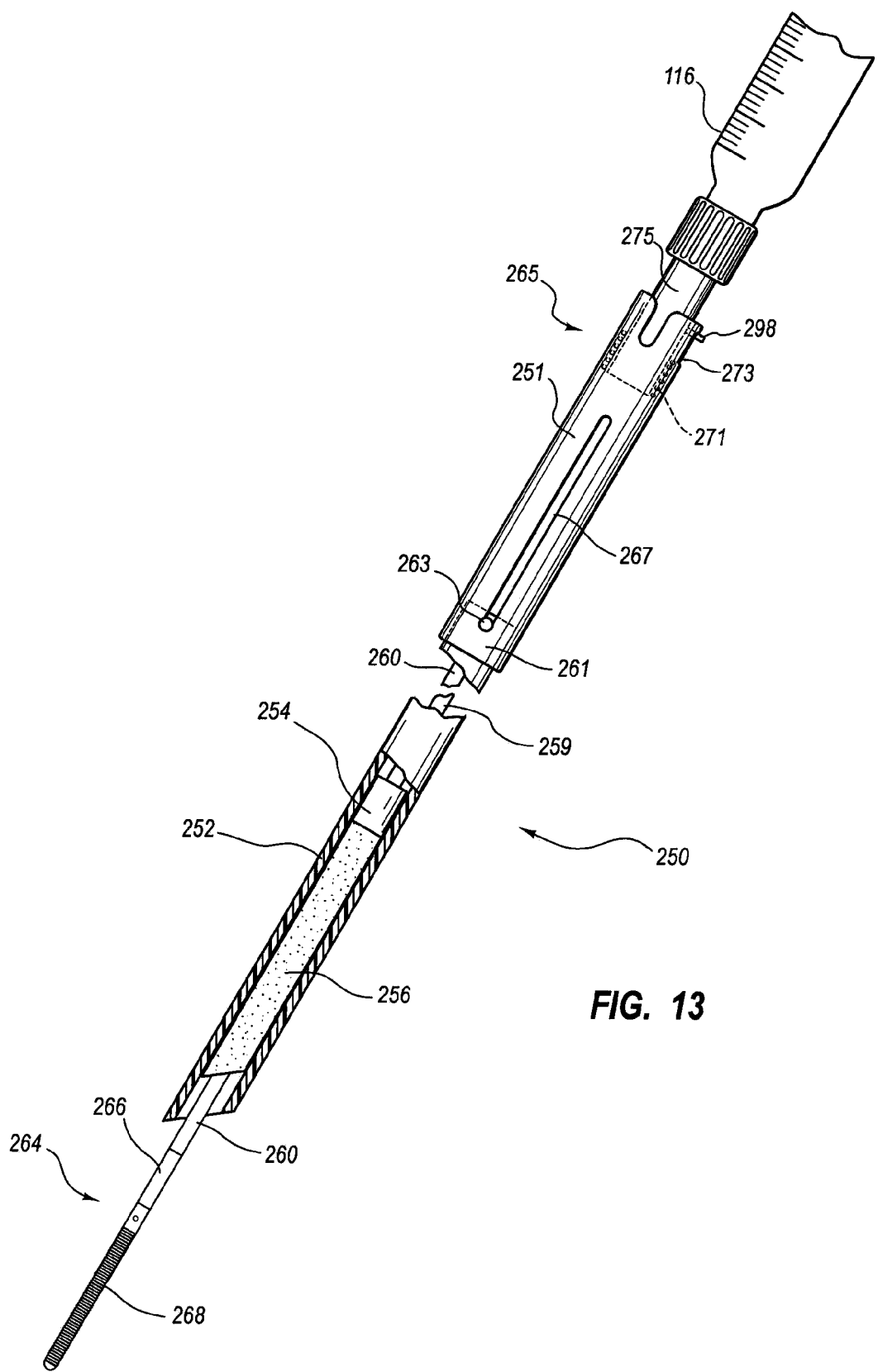
FIG. 13 shows a side view of another embodiment of a vascular closure device.

Referring to FIG. 13, one embodiment of the vascular closure device 250 is shown that may be used to close and/or seal a hole or puncture in a blood vessel such as an arteriotomy. The vascular closure device 250 has a distal end 264 and a proximal end 265 and includes a handle 251, a carrier tube or carrier member 252 (which may be referred to as an introducer sheath in some embodiments), sealing material 256, a stopper 254, and a vessel locator assembly or vessel locator portion 260. The vessel locator assembly 260 includes a central tube 259 that extends through the handle 251, the carrier tube 252, the stopper 254, and the sealing material 256. The vessel locator assembly 260 also includes an expandable portion 266 positioned at the distal end 264 of the vascular closure device 250 and a syringe 275 positioned at the proximal end 265 of the vascular closure device 250. The syringe 275 is coupled to and in fluid communication with the central tube 259.

The handle 251 is positioned at the proximal end 265 of the vascular closure device 250 and allows the user to manipulate the various components of the device 250 to facilitate closing the hole in the blood vessel. In the embodiment shown in FIG. 13, the handle 251 includes a first tube 261 having a distal end that is sized to slidably receive the carrier tube 252 and a proximal end that is sized to slidably receive a syringe 275. The first tube 261 includes a slot 267 that receives an actuation member, protrusion, or pin 263 that extends outward from the carrier tube 252. The user can reciprocally move the actuation member 263 proximally and distally in the slot 267 to retract and extend, respectively, the carrier tube 252. Retracting the carrier tube 252 when the vascular closure device 250 is deployed exposes the sealing material 256 to the tissue tract.

Returning to the vessel locator assembly 260, the syringe 275 may be used to selectively expand and/or contract the expandable portion 266. Any suitable fluid may be used to expand the expandable portion 266. For example, fluids such as saline solution, carbon dioxide, or air may be suitable. Also a guide wire and a spring 268 may be coupled proximally to the expandable portion 266. The guide wire and the spring 268 are configured to be atraumatic to prevent the distal end 264 of the vascular closure device 250 from puncturing or damaging the blood vessel.

The vascular closure device 250 is configured so that when it is inserted into the tissue tract, the expandable portion 266 is positioned inside the blood vessel. The expandable portion 266 may be configured to move between the contracted configuration shown in FIG. 13 and the expanded configuration shown in FIG. 15. This allows the expandable portion 266 to be inserted into the blood vessel, expanded, and then moved into contact with the interior wall of the blood vessel adjacent to the hole. The expandable portion 266 and the sealing material 256 are spaced apart a predetermined distance so that when the expandable portion 266 is positioned against the interior wall of the blood vessel, the sealing material 256 is positioned just outside of the hole in the blood vessel. In the embodiment shown in FIGS. 13-23, the expandable portion 266 includes a balloon that may use the same materials and/or otherwise be similar to the balloon described in connection with the expandable portion 114. For example, the expandable portion 266 may be positioned at an oblique angle like the expandable portion 114.

It should be appreciated that the central tube 259 and any of the other components of the vessel locator assembly 260 may be made of any suitable material such as metal, plastics, or composites. Since the vascular closure device 250 is a medical device, the materials used may also be medical grade (medical grade metals, plastics, or composites). In one embodiment, the central tube 259 may be made of metals such as stainless steel or memory shape metals such as nitinol, and the like.

The stopper 254 is provided to prevent the sealing material 256 from moving proximally as the carrier tube 252 moves proximally. Accordingly, the stopper 254 is positioned just proximal to the sealing material 256 inside the carrier tube 252 and the stopper 254 is coupled to the central tube 259 so that it is fixed in position.

Referring to FIG. 13, the vascular closure device 250 may be configured to indicate when the expandable portion 266 is in contact with the interior wall of the blood vessel. One problem associated with locating the wall of the blood vessel is that the user may be unable to feel when the expandable portion 266 has contacted the wall of the blood vessel. The user may continue to pull on the vascular closure device 250 causing it to distort and bend until it passes through the hole in the blood vessel or the expanded expandable portion 266 may tear through the hole in the wall of the blood vessel causing additional injury to the patient.

The first tube 261 and the syringe 275 are coupled together in a manner that signals to the user when the expanded expandable portion 266 is positioned against the interior wall of the blood vessel. The syringe 275 is positioned to move lengthwise in the first tube 261. The central tube 259 is coupled to the syringe 275 so that when the expandable portion 266 contacts the interior wall of the blood vessel, the tension on the central tube 259 pulls the syringe 275 further into the first tube 261. A spring 271 is positioned between the first tube 261 and the syringe 275 to bias the syringe 275 in the proximal direction and resistant the tension exerted by the core wire 270. The spring 271 is configured to provide just the right amount of force so that the spring 271 is only compressed, and consequently the syringe 275 moved, when the expandable portion 266 has contacted the interior wall of the blood vessel.

An indicator pin 298 extends outward from the syringe 275 and travels in a slot 273 in the first tube 261. As the spring 271 is compressed, the indicator pin 298 moves distally in the slot 273. In operation, the user can pull back on the vascular closure device 250 while watching the indicator pin 298. When the indicator pin 298 begins to move distally in the slot 273, the user knows that the expandable portion 266 is positioned against the interior wall of the blood vessel. The indicator pin 298 also prevents the spring 271 from biasing the syringe 275 out the proximal end of the first tube 261.

It should be appreciated that numerous other methods may be used to signal the user that the expandable portion 266 is positioned against the interior wall of the blood vessel. The signal may be visual, auditory, or any other suitable type of signal. In one embodiment, the vascular closure device 250 may be configured to emit a beep to alert the user that the expandable portion 266 is positioned against the interior wall of the blood vessel.

It should be appreciated that the design of the vascular closure devices 250 may be altered in any of a number of ways. For example, FIGS. 20-23 show another embodiment of the vascular closure device 250. In this embodiment, the vascular closure device 250 includes a perforated tube 292 that is used to dispense the sealing material 256 into the tissue tract. In one embodiment, the vascular closure device 250 may be provided with another syringe coupled to the proximal end of the perforated tube 292. The syringe may be used to inject the sealing material 256 out through the holes 293 in the perforated tube 292. The distal end of the perforated tube 292 may be blocked or closed so that the sealing material 256 is forced out the sides of the perforated tube 292 against the walls of the tissue tract instead of down against the hole, which may result in sealing material entering the blood stream.

Figure 21:
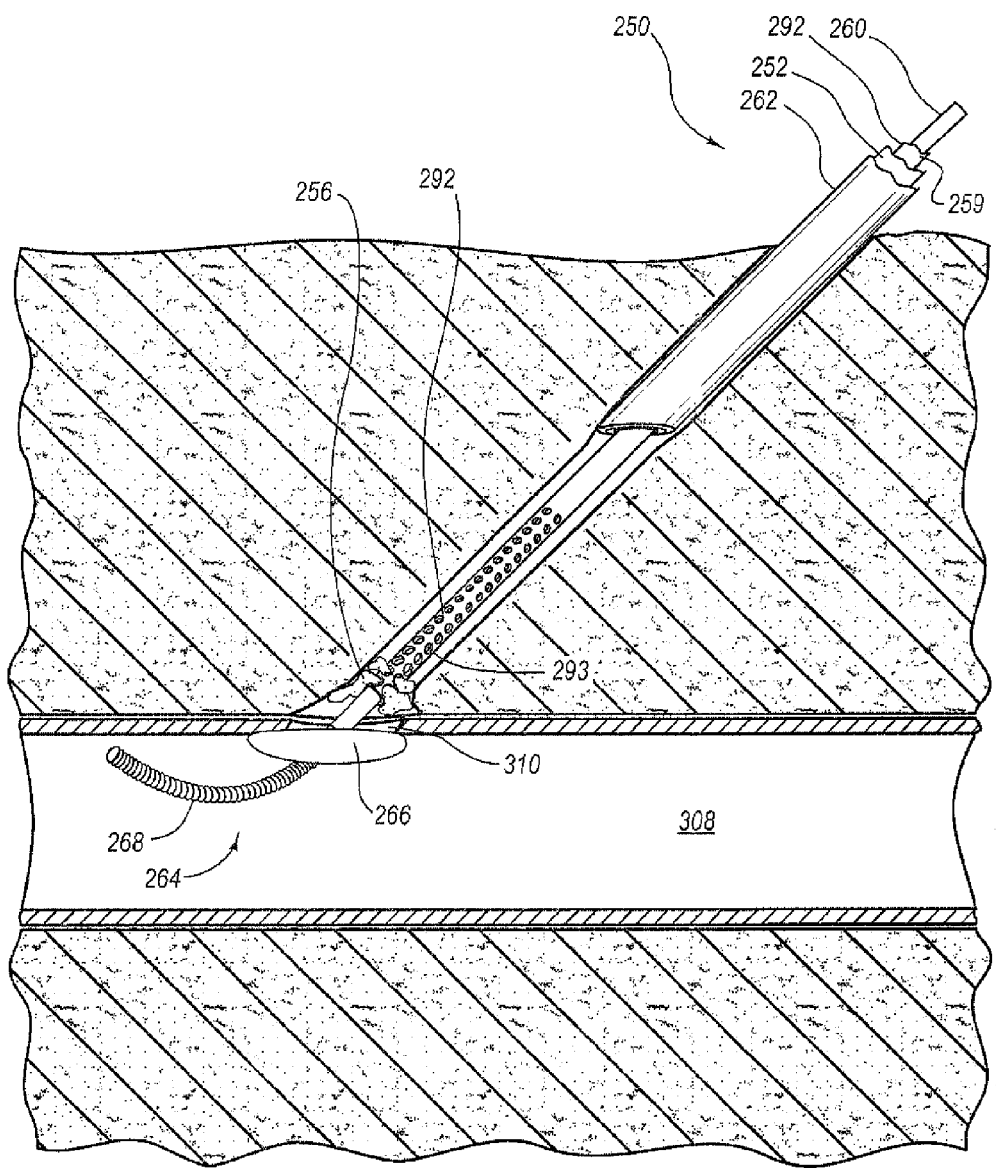
Figure 22:
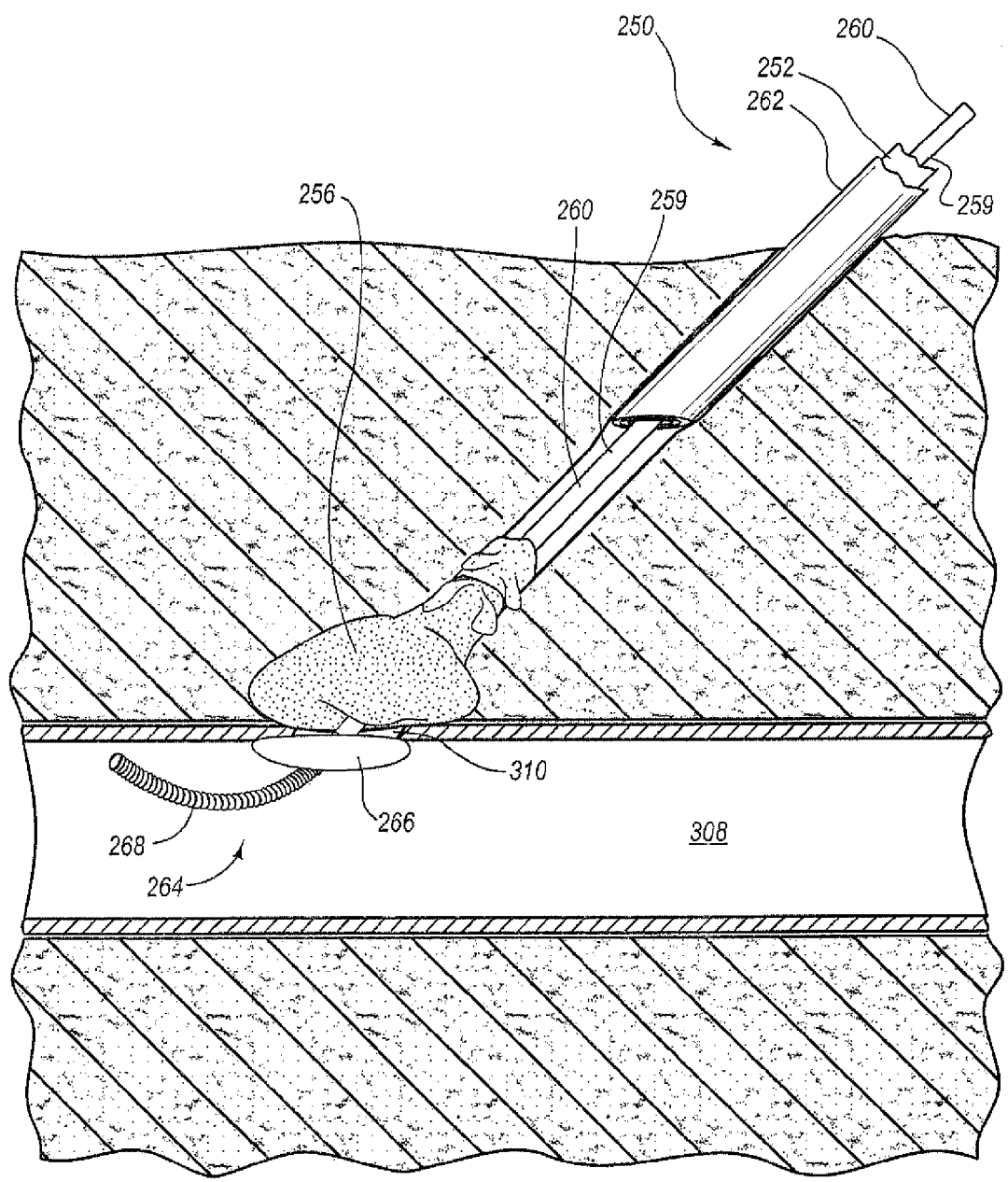
Figure 23:
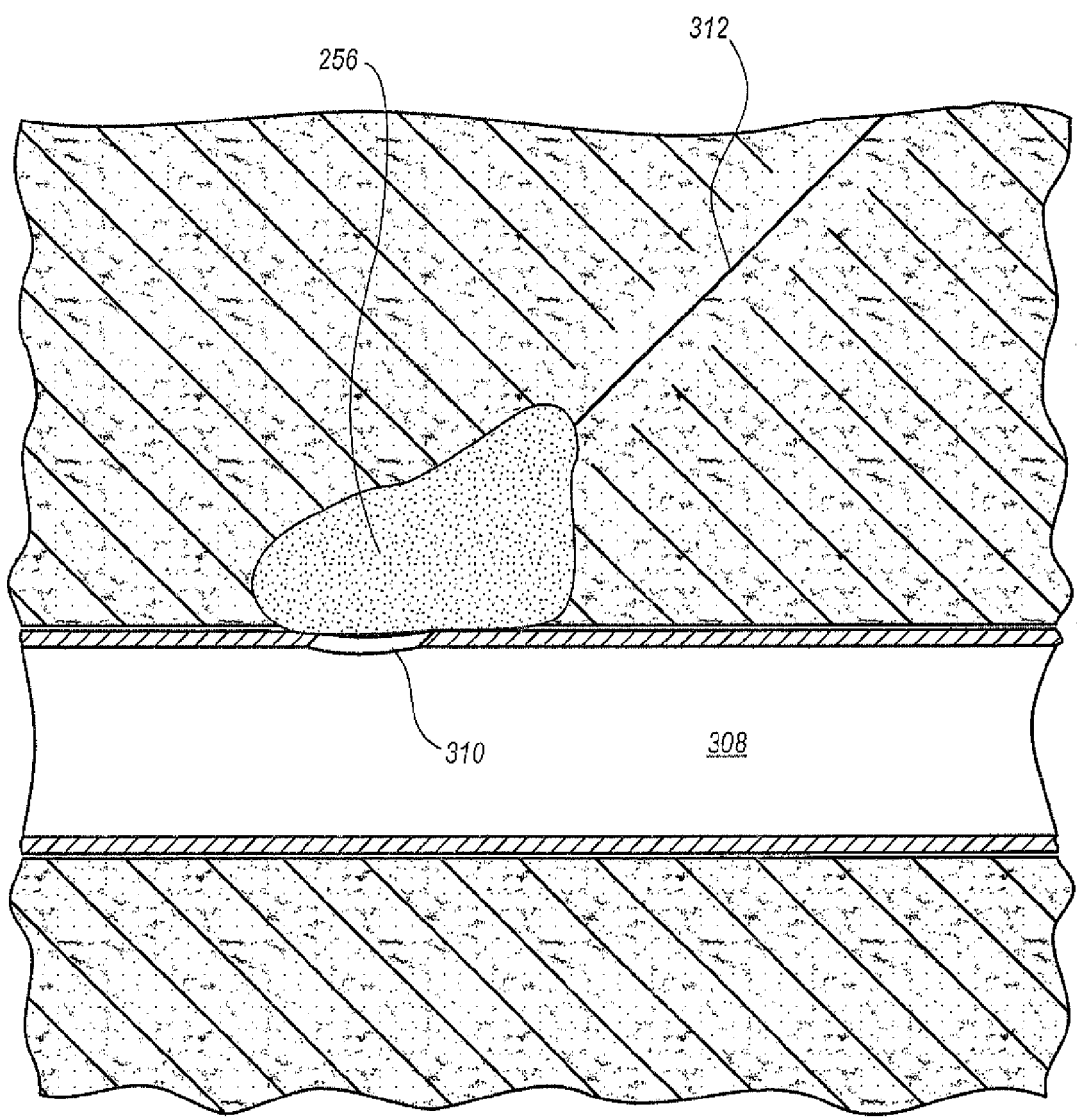

As shown in FIG. 21, the holes 293 in the perforated tube 292 may be sized to regulate the flow of the sealing material 256. For example, the holes 293 may get larger moving in a distal direction along the perforated tube 292 so that the largest holes 293 are positioned nearest the distal end of the perforated tube 292. This configuration results in an even amount of sealing material 256 being dispensed along the perforated tube 292. It should be appreciated that in other embodiments, the holes 293 may be configured to be the same size or all of the holes 293 may be unique sizes. Numerous configurations are possible.

A method of closing a hole 310 in a blood vessel 308 using the vascular closure device 250 is described in connection with FIGS. 14-23. Once the procedure is over and the user is ready to close the hole in the blood vessel, the initial step may be to exchange the procedural access sheath for the introducer sheath 262. This is done by placing a guidewire through the procedural sheath and into the blood vessel 308. The procedural sheath is then withdrawn from the body while holding digital pressure on the blood vessel 308, upstream from the sheath, and while holding the guidewire in place. Next, a closure dilator is placed within the introducer sheath 262 and the distal tapered end of the closure dilator is back-loaded onto the guidewire. The closure dilator and the introducer sheath 262 are advanced together distally over the guidewire, through the tissue tract 312, and into the blood vessel 308.

In one embodiment, the introducer sheath 262 includes a distal side hole (not shown) near the distal end of the introducer sheath 262. The closure dilator also includes a distal side hole that is configured to align with the distal side hole in the introducer sheath 262 when the closure dilator is positioned in the introducer sheath 262. The closure dilator also has a proximal side hole at the proximal end of the closure dilator that is in fluid communication with the distal side hole of the closure dilator and the closure sheath. In one embodiment, the distal and proximal side holes may be fluidly connected by way of a dedicated lumen or bore. In another embodiment, the distal and proximal side holes may be fluidly connected by the central lumen of the closure dilator that the guidewire is positioned in.

The distal and proximal side holes in the introducer sheath 262 and the closure dilator are provided to allow blood to flash back when the introducer sheath 262 is correctly positioned in the blood vessel 308. Once blood flows out the proximal side hole of the closure dilator, the user pulls the introducer sheath 262 in a proximal direction until the blood flow just stops. The introducer sheath 262 is now placed in the correct position to continue the procedure. The next step is to withdraw the closure dilator and the guidewire while holding the introducer sheath 262 in place.

The introducer sheath 262 is sized to slidably receive the vascular closure device 250 therein. The distal ends of the introducer sheath 262 and the carrier tube 252 have a tapered shape so that the tip will align with the lengthwise axis of the blood vessel 308 when the introducer sheath 262 is inserted through the tissue tract 312 at an angle of about 20-45 degrees to the vessel axis.

Figure 14:
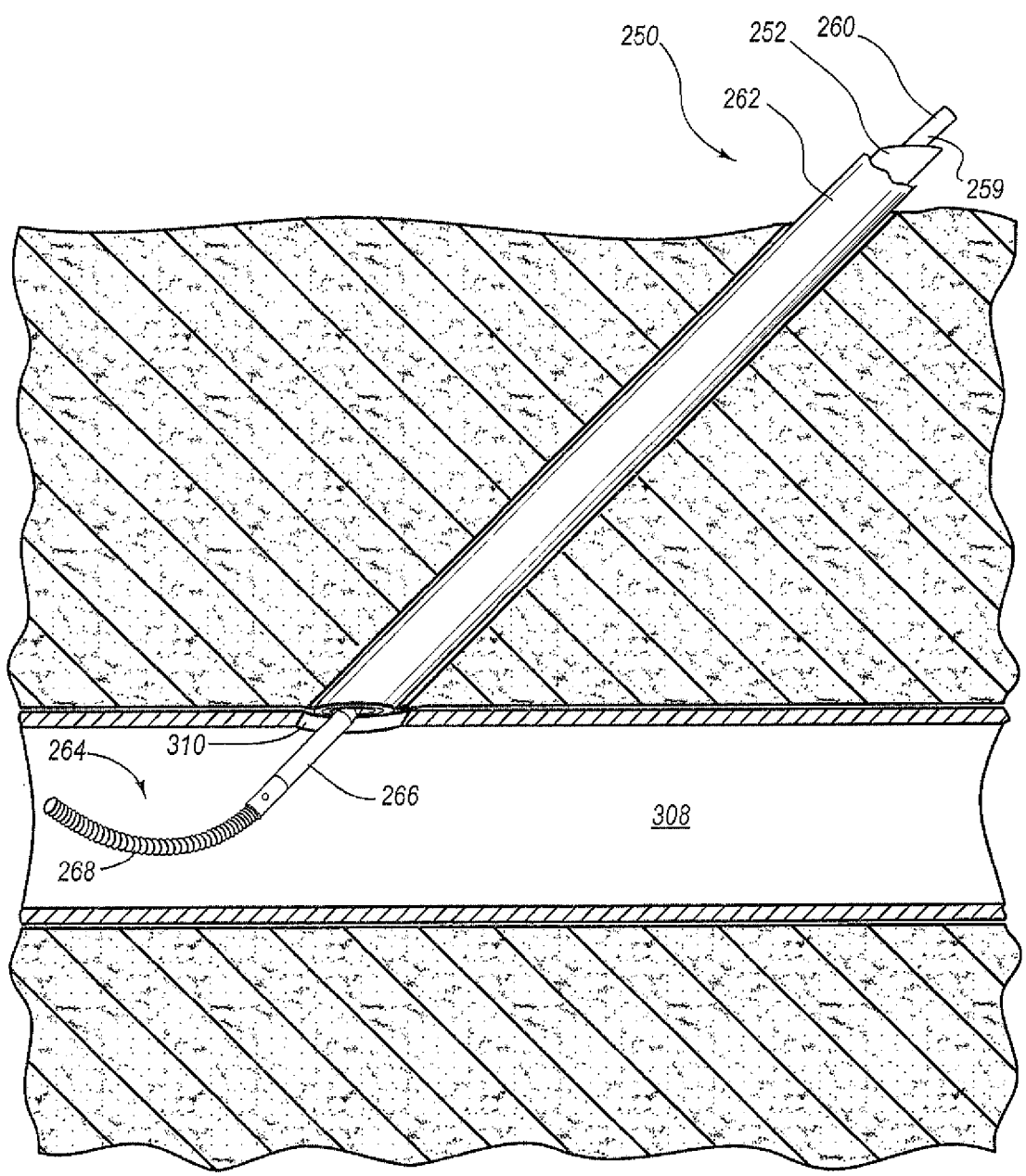
FIG. 14 shows the vascular closure device from FIG. 13 inserted into a blood vessel.
Figure 15:
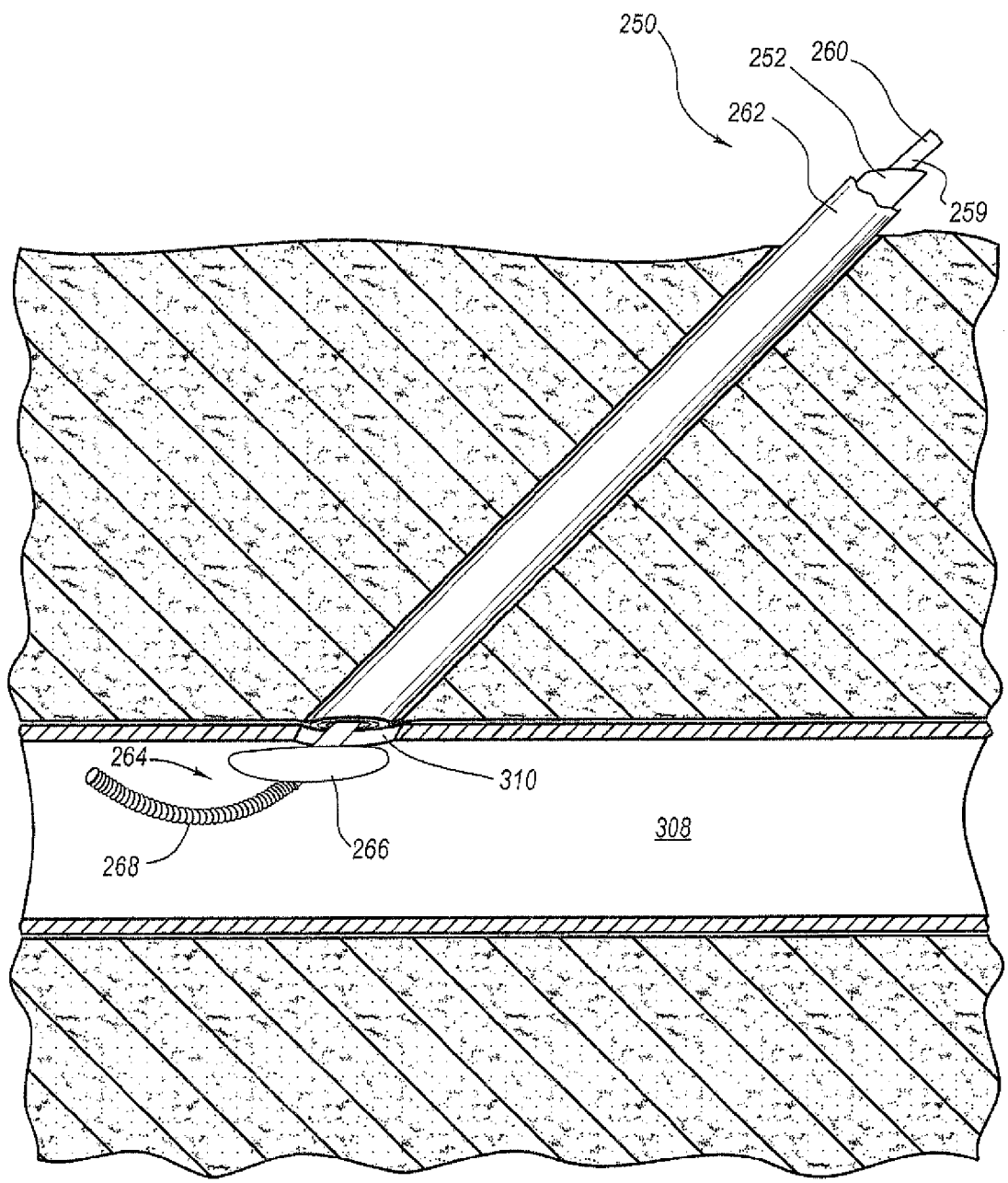
FIG. 15 shows the vascular closure device from FIG. 13 inserted into the blood vessel with a expandable portion in an expanded configuration and spaced apart from the interior wall of the blood vessel.
Figure 16:
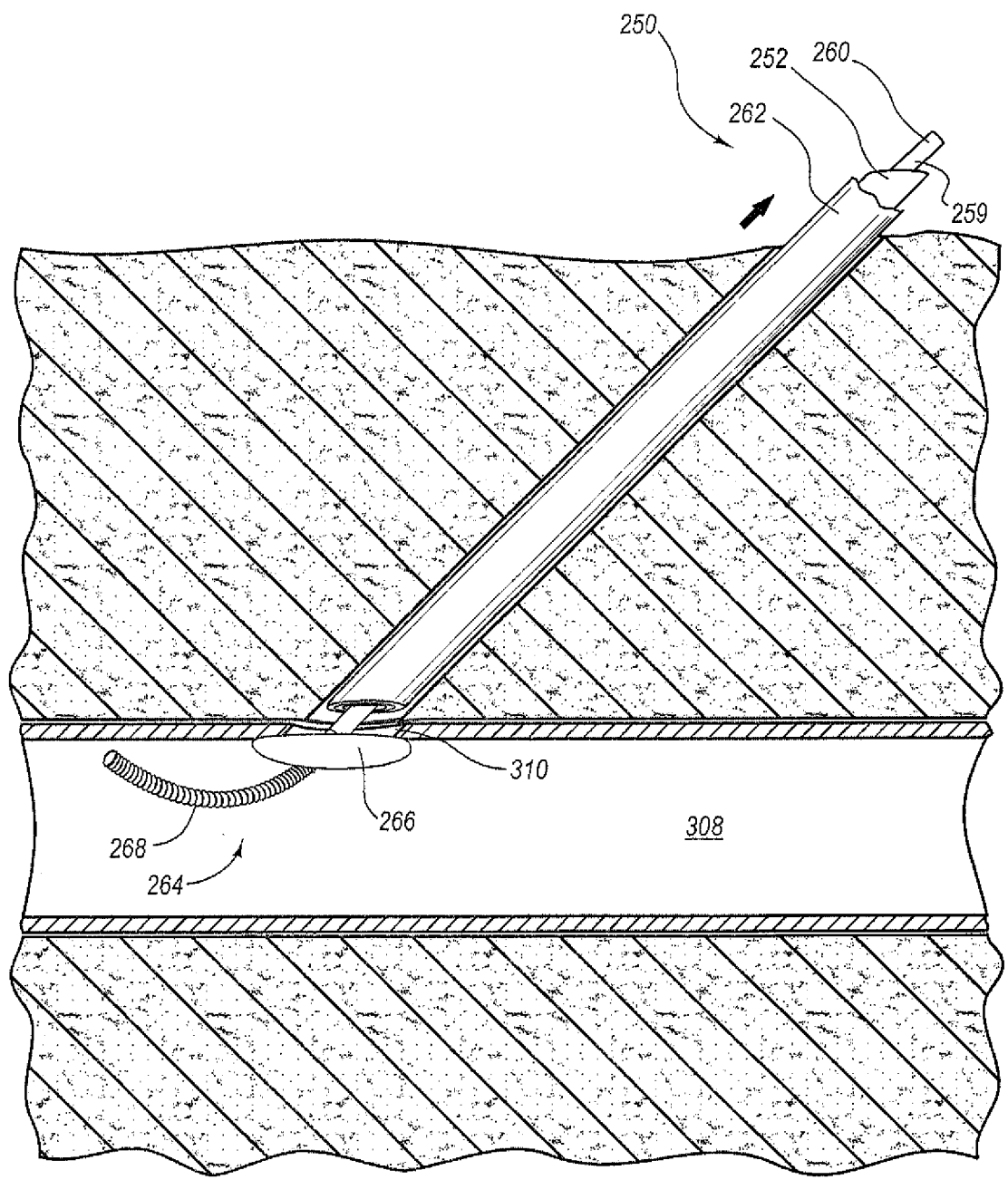
FIG. 16 shows the vascular closure device from FIG. 13 with the expandable portion positioned up against the interior wall of the blood vessel.

After the introducer sheath 262 is in place, the vascular closure device 250 is introduced into the proximal end of the introducer sheath 262. The vascular closure device 250 may be configured to advance until it snaps, locks, or otherwise mates together with the carrier tube 62. In this position, the distal end 264 of the vascular closure device 250 extends out of the distal end of the introducer sheath 262 and into the blood vessel 308. It should be noted that the vascular closure device 250 and the introducer sheath 262 may be configured so that when they are coupled together, the distal end 264 extends into the blood vessel 308 a predetermined amount, FIG. 14 shows the expandable portion 266 in position in the blood vessel 308. The expandable portion 266 is expanded using the syringe 275. FIG. 15 shows the expandable portion 266 in the expanded configuration. The introducer sheath 262 and the vascular closure device 250 are drawn away from the patient until the expandable portion 266 contacts the vessel wall at the puncture site as shown in FIG. 16.

Figure 17:
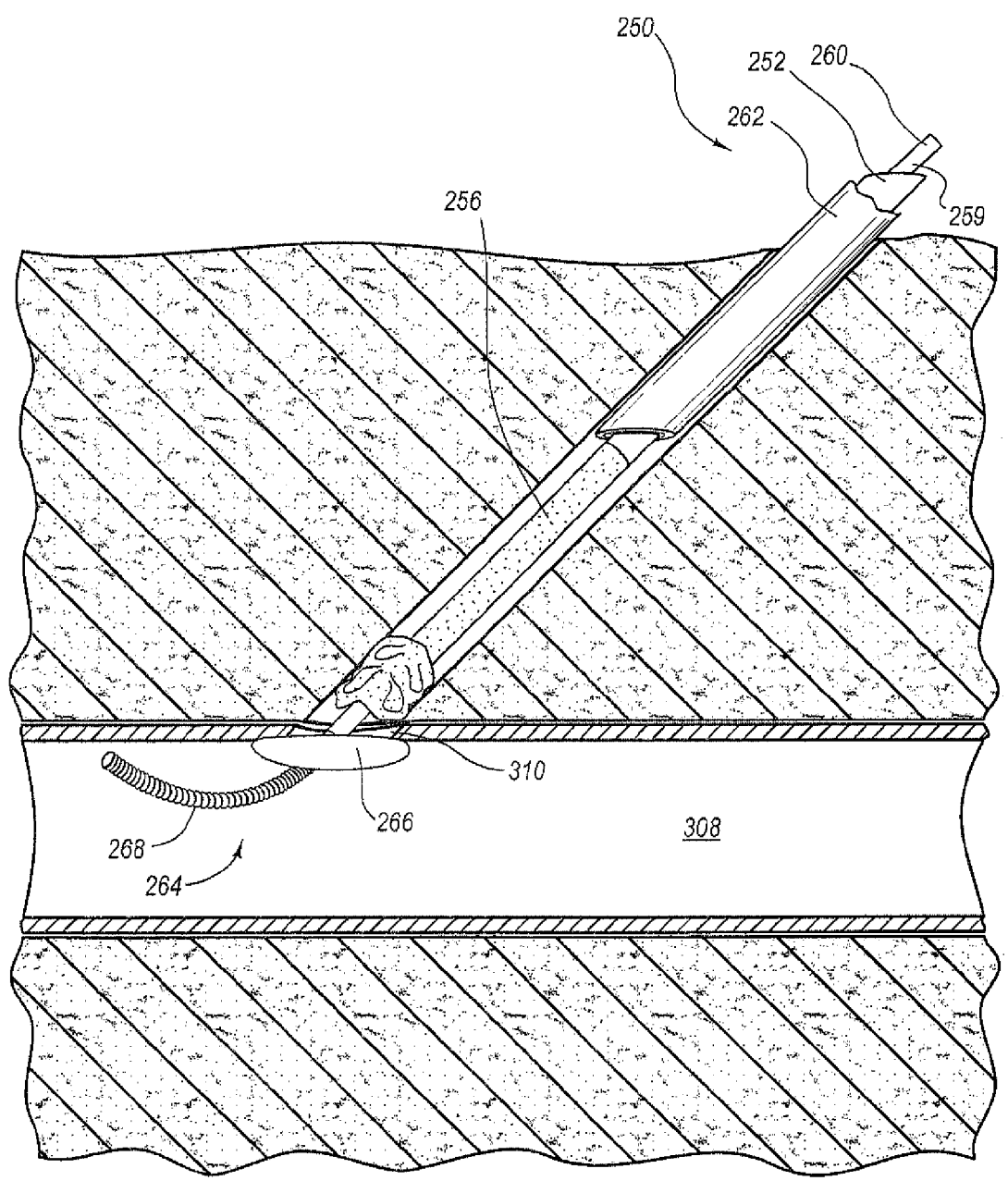
FIG. 17 shows the vascular closure device from FIG. 13 with the carrier tube and insertion sheath retracted to expose the sealing material to the tissue tract. The sealing material is beginning to change phase and fill in the tissue tract.
Figure 18:
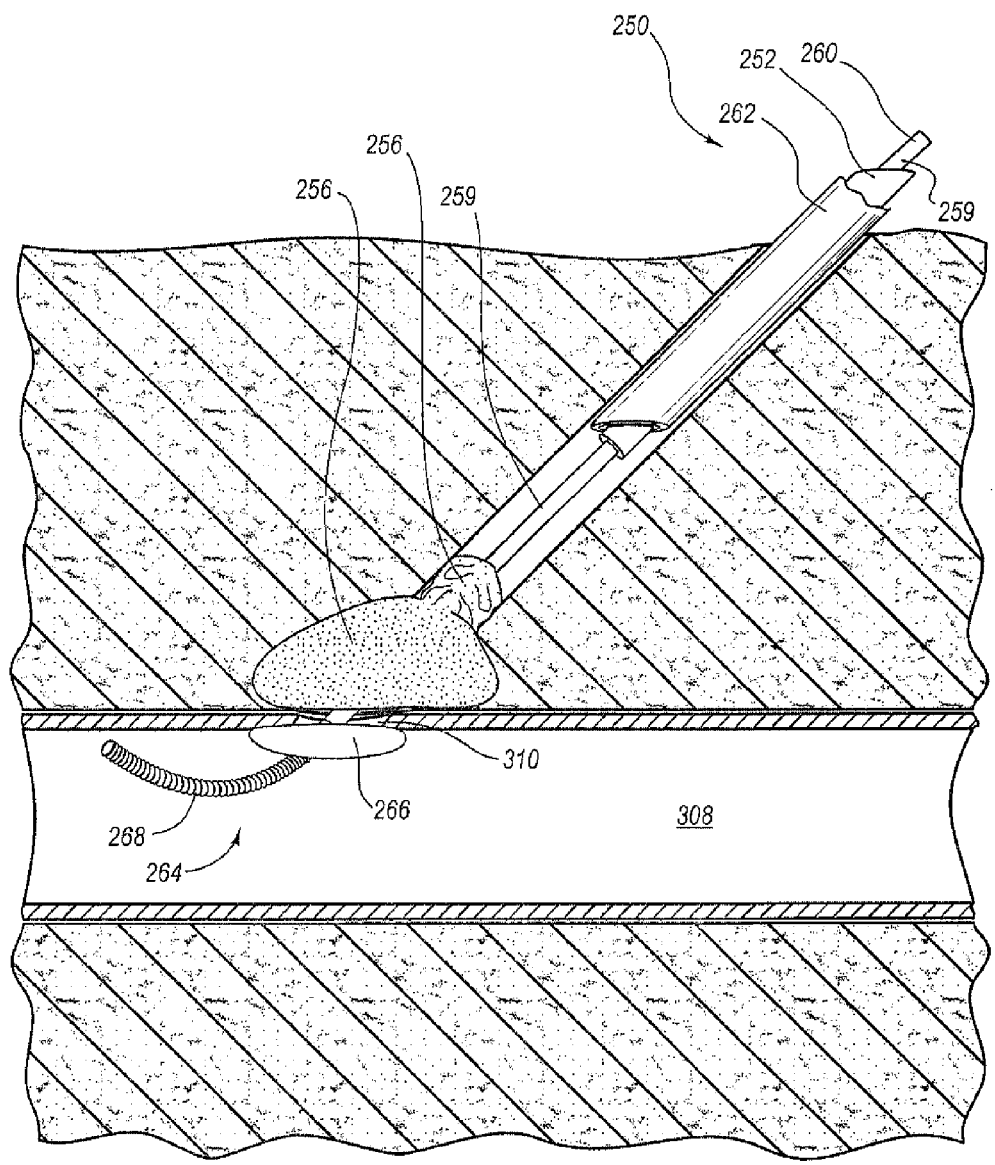
FIG. 18 shows the sealing material as it changes from a liquid/gel to a cubic phase.
Figure 19:
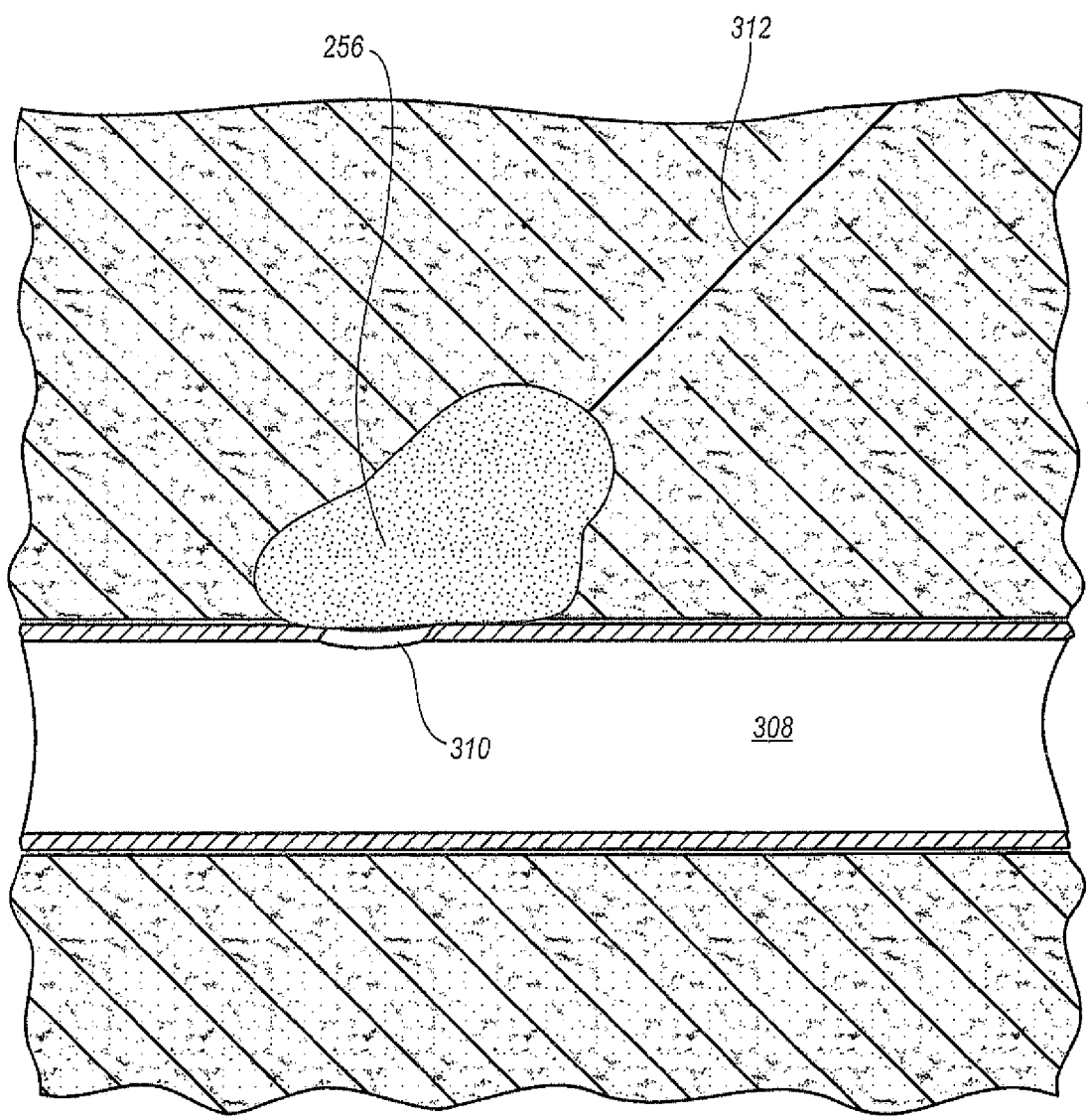
FIG. 19 shows the sealing material deployed adjacent to the hole in the blood vessel after the vascular closure device from FIG. 13 has been removed.
Figure 20:
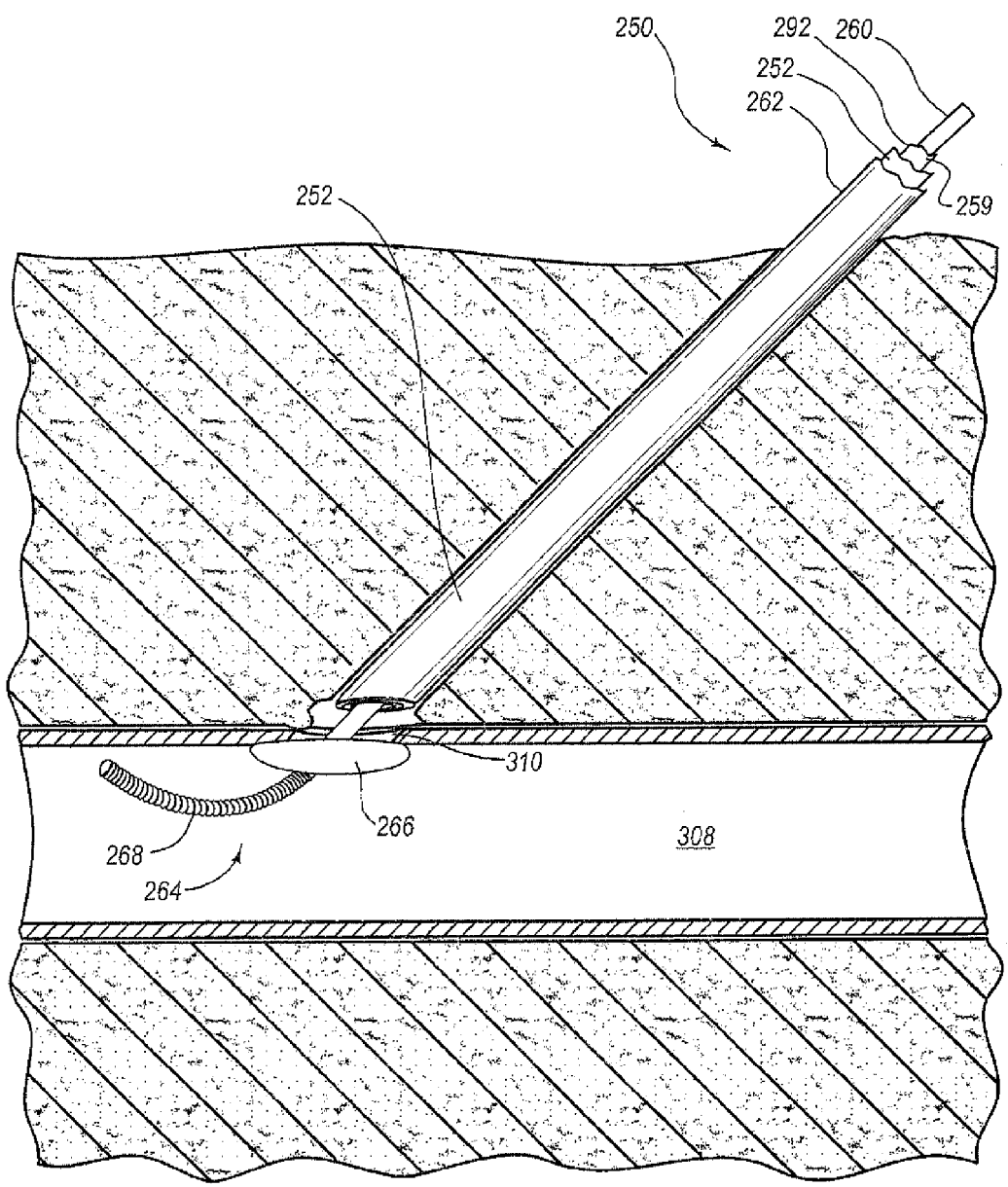
FIGS. 20-23 show another embodiment of the vascular closure device that uses a perforated tube to inject the scaling material into the tissue tract.

Now that the expandable portion 266 is in position, the introducer sheath 262 and the carrier tube 252 are withdrawn to expose the sealing material 256 to the tissue tract 312. The sealing material begins to melt as it is heated by the body and flows down toward the hole 310 in the blood vessel 308 as shown in FIG. 17. The expandable portion 266 blocks the hole 310 so that the sealing material 256 does not flow into the bloodstream. The sealing material 256 begins to form a cubic phase upon exposure to bodily fluids such as blood and the like. This causes the sealing material 256 to expand and fill the tissue tract 312 adjacent to the hole 310 in the blood vessel 308 as shown in FIG. 18. It should be appreciated that the vascular closure device 250 may be configured to use a second non-flowable sealing material or anchor along with the sealing material 256. For example, the vascular closure device 250 may be configured to deposit a small collagen plug adjacent to the hole 310 to prevent the sealing material 256 from entering the blood vessel 308.

Now that the sealing material 256 has been deployed and has formed the solid or somewhat firm cubic phase, the next step is to contract the expandable portion 266 and withdraw the vessel locator assembly 260 and the remainder of the vascular closure device 250 from the tissue tract 312. As the vessel locator assembly 260 passes through the sealing material 256, the sealing material 256 swells or otherwise moves to fill the gap where the vessel locator assembly 260 used to be. The hole in the blood vessel 308 is now sealed by clotting action and the sealing material 256 positioned in the tissue tract 312.

The method of using the vascular closure device 250 shown in FIGS. 20-23 is similar to the method of using the vascular closure device 250 shown in FIGS. 14-19. However, instead of passively allowing the sealing material 256 to melt and fill the tissue tract 312, the user can inject any desired amount of sealing material 256 into the tissue tract 312 through the perforated tube 292. This allows for additional sealing material 256 to be deployed. Also, the user may inject sealing material 256 through the perforated tube 292 as the perforated tube 292 is being withdrawn so that the sealing material fills up the entire tissue tract 312.

It should be appreciated that the embodiments disclosed have many components and the methods described have many steps for operation and use. It is anticipated that the number of components and steps could be altered considerably without departing from the broad scope of what is described herein.

Illustrative Embodiments

Reference is made in the following to a number of illustrative embodiments of the subject matter described herein. The following embodiments illustrate only a few selected embodiments that may include the various features, characteristics, and advantages of the subject matter as presently described. Accordingly, the following embodiments should not be considered as being comprehensive of all of the possible embodiments. Also, features and characteristics of one embodiment may and should be interpreted to equally apply to other embodiments or be used in combination with any number of other features from the various embodiments to provide further additional embodiments, which may describe subject matter having a scope that varies (e.g., broader, etc.) from the particular embodiments explained below. Accordingly, any combination of any of the subject matter described herein is contemplated.

According to one embodiment, a method of closing a hole in a vessel of a patient, comprises: moving an expandable portion of a vascular closure device through the hole and into the vessel, the vascular closure device including a main body that extends through the hole at an oblique angle relative to the vessel; expanding the expandable portion of the vascular closure device; and moving the expandable portion into contact with an inner wall of the vessel to block the hole, the expandable portion being oriented at least substantially parallel to the inner wall of the vessel shortly before contacting the inner wall. The method may comprise applying a sealing material to the hole while the expandable portion is in contact with the inner wall of the vessel. The sealing material may include a sealant. The sealant may be applied using suction. The method may comprise applying a sealing material to the hole while the expandable portion is in contact with the inner wall of the vessel; contracting the expandable portion; and removing the expandable portion of the vascular closure device from the vessel. The method may comprise applying manual pressure to the hole after removing the expandable portion of the vascular closure device from the vessel. The vessel may include a blood vessel. The expandable portion may be oriented at an oblique angle relative to the main body shortly before contacting the inner wall. The expandable portion may be made, at least in part, of polyurethane. The expandable portion may include a tail. Moving the expandable portion of the vascular closure device through the hole and into the vessel may include moving the expandable portion through an introducer that extends into the vessel.

According to another embodiment, a method of closing a hole in a vessel of a patient, comprises: expanding an expandable portion of a vascular closure device inside the vessel, the expandable portion being oriented at an oblique angle relative to a main shaft of the vascular closure device; and moving the expandable portion into contact with an inner wall of the vessel to block the hole. The method may comprise applying a sealing material to the hole while the expandable portion is in contact with the inner wall of the vessel. The sealing material may include a sealant. The sealant may be applied using suction. The method may comprise applying a sealing material to the hole while the expandable portion is in contact with the inner wall of the vessel; contracting the expandable portion; and removing the expandable portion of the vascular closure device from the vessel. The method may comprise applying manual pressure to the hole after removing the expandable portion of the vascular closure device from the vessel. The vessel may include a blood vessel such as an artery. The expandable portion may be made, at least in part, of polyurethane. The expandable portion may include a tail. The method may comprise moving the expandable portion of the vascular closure device through an introducer that extends into the vessel.

According to another embodiment, a method of closing a hole in a blood vessel of a patient comprises: expanding an expandable portion of a vascular closure device inside the blood vessel, the expandable portion being oriented at an oblique angle relative to a main shaft of the vascular closure device; moving the expandable portion into contact with an inner wall of the vessel to block the hole; applying a sealing material to the hole while the expandable portion is in contact with the inner wall of the blood vessel; contracting the expandable portion; and removing the expandable portion of the vascular closure device from the blood vessel. The sealing material may include a sealant. The expandable portion may include a tail.

According to another embodiment, a vascular closure device comprises: a main body having a distal end; and an expandable portion positioned at the distal end of the main body, the expandable portion being configured to be inserted into a hole in a vessel of a patient; wherein the expandable portion is oriented at an oblique angle relative to the main body when the expandable portion is in an expanded configuration. The main body may form a conduit that is in fluid communication with the expandable portion, the expandable portion being selectively expandable with fluid delivered by the conduit. The main body may include hypotube that forms the conduit. The main body may include a guidewire. The expandable portion may be attached to the guidewire. The guidewire may include hypotube to deliver fluid to the expandable portion. The vascular closure device may comprise a conduit to deliver sealant to an area adjacent to the expandable portion. The expandable portion may be positioned adjacent to a distal tip of the main body. The expandable portion may extend outward from a distal tip of the main body. The expandable portion may be oriented at an angle of approximately 20° to 70° relative to the main body when the expandable portion is in the expanded configuration. The expandable portion may be made, at least in part, of polyurethane. The expandable portion may include a tail.

According to another embodiment, a vascular closure device comprises: a guidewire; and an expandable portion attached to the guidewire; wherein the expandable portion is configured to be inserted into a vessel of a patient through a hole in a wall of the vessel, the vascular closure device being configured to close the hole in the wall of the vessel.

According to another embodiment, a vascular closure device comprises: a cylindrical tube; and an expandable portion attached to the cylindrical tube; wherein the expandable portion is configured to be inserted into a vessel of a patient through a hole in a wall of the vessel, the vascular closure device being configured to close the hole in the wall of the vessel.

According to another embodiment, a vascular closure device comprises an expandable portion made at least in part of polyurethane, the expandable portion being configured to be inserted into a vessel of a patient through a hole in a wall of the vessel, the vascular closure device being configured to close the hole in the wall of the vessel.

According to another embodiment, an internal tissue puncture sealing apparatus comprises a first thin, elongated conduit having a first central lumen and first and second ends. The first end may be insertable through the internal tissue puncture and has an inflation segment in fluid communication with the central lumen. The first end may include an expandable member that is selectively inflatable with a fluid via the central lumen. The apparatus may also include a second thin, elongated conduit having a second central lumen receptive of the first thin, elongated conduit. The proximal end of the second conduit has at least one valved side-port in fluid communication with a space between the first and second conduits. The valved side-port may include a vacuum communication path and a sealant injection path, which enable aspiration of a tissue puncture site and sealing of the puncture.

According to another embodiment, a method of closing a hole in a vessel wall may include inserting an inflatable device through an introducer that is disposed in the vessel, inflating the inflatable device, sealing the inflatable device against an inner wall of the vessel, reducing the pressure inside of the introducer, injecting a sealant into the introducer, deflating the inflatable device, and removing the inflatable device through the sealant. Following removal of the inflatable device, manual pressure may be applied to the hole for a short period of time to ensure continued hemostasis. A specially designed introducer may be swapped with a standard introducer used to facilitate insertion of vascular tools used to perform a vascular procedure prior to inserting the inflatable device.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

As used herein, spatial or directional terms, such as "left," "right," "front," "back," and the like, relate to the subject matter as it is shown in the drawing FIGS. However, it is to be understood that the subject matter described herein may assume various alternative orientations and, accordingly, such terms are not to be considered as limiting. Furthermore, as used herein (i.e., in the claims and the specification), articles such as "the," "a," and "an" can connote the singular or plural. Also, as used herein, the word "or" when used without a preceding "either" (or other similar language indicating that "or" is unequivocally meant to be exclusive—e.g., only one of x or y, etc.) shall be interpreted to be inclusive (e.g., "x or y" means one or both x or y). Likewise, as used herein, the term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A vascular closure device comprising:
   a main body having a distal end;
   an expandable portion positioned at the distal end of the main body, the expandable portion being configured to be inserted into a hole in a blood vessel of a patient;
   an introducer sheath extending around the main body;
   a tube extending around the introducer sheath;
   a pin extending outward from the main body through the tube;
   wherein the expandable portion is oriented at an oblique angle relative to the main body when the expandable portion is in an expanded configuration prior to contact with an internal wall of the blood vessel, the expandable portion completely sealing the hole upon contact with the internal wall;
   wherein the main body and expandable portion, when extending through the introducer sheath, restrict passage of other devices through the introducer sheath;
   wherein the main body terminates at the expandable portion.

2. The vascular closure device of claim 1 wherein the main body forms a conduit that is in fluid communication with the expandable portion, the expandable portion being selectively expandable with fluid delivered by the conduit.

3. The vascular closure device of claim 2 wherein the main body includes a hypotube that forms the conduit.

4. The vascular closure device of claim 2 further comprising a guidewire that extends distally from the expandable portion.

5. The vascular closure device of claim 1 wherein the introducer sheath is to deliver sealing material to an area proximal to the expandable portion.

6. The vascular closure device of claim 1 wherein the expandable portion is oriented at an angle of approximately 20° to 45° relative to the main body when the expandable portion is in the expanded configuration.

7. The vascular closure device of claim 1 wherein the expandable portion comprises a resilient elastomeric material.

8. The vascular closure device of claim 1, wherein the expandable portion defines a distal most point of the vascular closure device.

9. A vascular closure device comprising:
a main body having a distal end;
an expandable portion positioned at the distal end of the main body, the expandable portion being insertable through a hole formed in a sidewall of a blood vessel;
an introducer sheath extending around the main body;
a tube positioned around the introducer sheath;
a pin extending outward from the main body and through the tube;
wherein the expandable portion is oriented at an oblique angle relative to the main body when in a rest state before contact with the sidewall of the blood vessel, the expandable portion completely sealing the hole upon contact with the sidewall;
wherein the main body and expandable portion, when extending through the introducer sheath, restrict passage of other devices through the introducer sheath;
wherein the main body terminates at the expandable portion.

10. The vascular closure device of claim 9 wherein the main body forms a conduit that is in fluid communication with the expandable portion, the expandable portion being selectively expandable with fluid delivered by the conduit.

11. The vascular closure device of claim 10 wherein the main body includes a hypotube that forms the conduit.

12. The vascular closure device of claim 10 further comprising a guidewire that extends distally from the expandable portion.

13. The vascular closure device of claim 9 wherein the introducer sheath is configured to deliver sealing material to an area proximal to the expandable portion.

14. The vascular closure device of claim 9 wherein the expandable portion is oriented at an angle of approximately 20° to 45° relative to the main body when the expandable portion is in an expanded configuration.

15. The vascular closure device of claim 9 wherein the expandable portion comprises a resilient elastomeric material.

16. A vascular closure device comprising:
a main body having a distal end;
an expandable portion positioned at the distal end of the main body and arranged at a first oblique angle relative to the main body;
an introducer sheath extending around the main body;
a tube through which the introducer sheath extends;
a pin extending from the main body through the tube;
wherein the vascular closure device is insertable through a hole formed in a sidewall of a blood vessel with the main body arranged at a second oblique angle relative to the sidewall, and a proximal surface of the expandable portion is arranged parallel with the sidewall without contacting the sidewall, the proximal surface completely sealing the hole upon contact with the sidewall;
wherein the main body and expandable portion, when extending through the introducer sheath, restrict passage of other devices through the introducer sheath;
wherein the main body terminates at the expandable portion.

17. The vascular closure device of claim 16 wherein the main body forms a conduit that is in fluid communication with the expandable portion, the expandable portion being selectively expandable with fluid delivered by the conduit.

18. The vascular closure device of claim 17 wherein the main body includes a hypotube that forms the conduit.

19. The vascular closure device of claim 16 wherein the introducer sheath is configured to deliver sealing material to an area proximal to the expandable portion.

20. The vascular closure device of claim 16 wherein the expandable portion is oriented at an angle of approximately 20° to 45° relative to the main body when the expandable portion is in an expanded configuration.

21. The vascular closure device of claim 16 wherein the expandable portion comprises a resilient elastomeric material.

* * * * *